United States Patent [19]
Dorziotis et al.

[11] Patent Number: 6,046,333
[45] Date of Patent: Apr. 4, 2000

[54] CONVERGENT PROCESS FOR THE PREPARATION OF A GROWTH HORMONE SECRETAGOGUE

[75] Inventors: Ilias Dorziotis, Bridgewater; Ioannis Houpis, Plainfield; Audrey Molina, Clark; Ralph Volante, Cranbury, all of N.J.

[73] Assignee: Merck & Co., Inc., Rahway, N.J.

[21] Appl. No.: 08/955,124

[22] Filed: Oct. 21, 1997

Related U.S. Application Data

[60] Provisional application No. 60/029,454, Oct. 25, 1996.

[51] Int. Cl.$^7$ .................................................. C07D 401/00
[52] U.S. Cl. .............................................................. 546/18
[58] Field of Search ................................................ 546/18

[56] References Cited

U.S. PATENT DOCUMENTS

| | | | |
|---|---|---|---|
| 5,536,716 | 7/1996 | Chen et al. | 514/215 |
| 5,723,616 | 3/1998 | Houghton et al. | 546/18 |

FOREIGN PATENT DOCUMENTS

| | | |
|---|---|---|
| WO 94/13696 | 6/1994 | WIPO . |
| WO 94/29309 | 12/1994 | WIPO . |
| WO 97/15574 | 5/1997 | WIPO . |

OTHER PUBLICATIONS

N. Sole, et al., *Tetrahedron* vol. 42, No. 1, pp. 193–198 (1986) "Mixed Anhydrides in Peptide Synthesis, Factors Affecting Urethane Formation and Racemization".

Sumitomo Seiyaku, *Derwent Abst.* 94–077374, (1994) "Cell Adhesion Peptide—for Suppression of Cancer Metastasis and Platelet Aggregation" (Japan).

Ioannis Houpis, et al., Presentation at Gordon Res. Conf. New Hmpton, NH, Jul. 14, 1996, "Synthesis of the Orally Active Nonpeptidal Growth Hormone Secretagogue, MK–677".

A. A. Patchett, et al., *Proc. Natl. Acad, Sci., USA*, vol. 92, pp. 7001–7005, (1995), "Design and Biological Activities of L–163–191 (MK–067): A Potent, Orally Active Growth Hormone Secretagogue".

*Primary Examiner*—D. Margaret Seaman
*Attorney, Agent, or Firm*—J. Eric Thies; David L. Rose

[57] ABSTRACT

The present invention is directed to a novel convergent process for the preparation of the compound N-[1(R)-[(1,2-dihydro-1-methanesulfonyl-spiro[3H-indole-3,4'-piperdin]-1'-yl)carbonyl]-2-(phenylmethyl-oxy)ethyl]-2-amino-2-methyl-propanamide, and salts thereof, which has the structure:

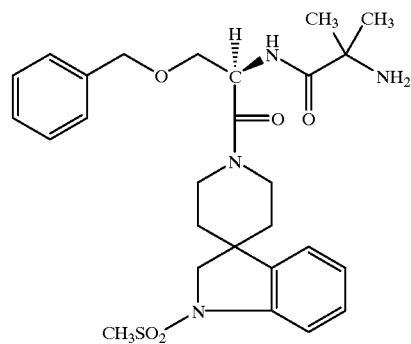

and which has the ability to stimulate the release of natural or endogenous growth hormone. This compound may be used to treat conditions which require the stimulation of growth hormone production or secretion such as in humans with a deficiency of natural growth hormone or in animals used for food or wool production where the stimulation of growth hormone will result in a larger, more productive animal.

25 Claims, No Drawings

CONVERGENT PROCESS FOR THE PREPARATION OF A GROWTH HORMONE SECRETAGOGUE

This application claims priority to Provisional Application Ser. No. 60/029,454, filed Oct. 25, 1996.

BACKGROUND OF THE INVENTION

Growth hormone, which is secreted from the pituitary, stimulates growth of all tissues of the body that are capable of growing. In addition, growth hormone is known to have the following basic effects on the metabolic processes of the body: (1) Increased rate of protein synthesis in all cells of the body; (2) Decreased rate of carbohydrate utilization in cells of the body; (3) Increased mobilization of free fatty acids and use of fatty acids for energy. A deficiency in growth hormone secretion can result in various medical disorders, such as dwarfism.

Various ways are known to release growth hormone. For example, chemicals such as arginine, L-3,4-dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase the secretion of the known secretagogue growth hormone releasing factor (GRF) or an unknown endogenous growth hormone-releasing hormone or all of these.

In cases where increased levels of growth hormone were desired, the problem was generally solved by providing exogenous growth hormone or by administering GRF or a peptidal compound which stimulated growth hormone production and/or release. In either case the peptidyl nature of the compound necessitated that it be administered by injection. Initially the source of growth hormone was the extraction of the pituitary glands of cadavers. This resulted in a very expensive product and carried with it the risk that a disease associated with the source of the pituitary gland could be transmitted to the recipient of the growth hormone. Recombinant growth hormone has become available which, while no longer carrying any risk of disease transmission, is still a very expensive product which must be given by injection or by a nasal spray. Other compounds have been developed which stimulate the release of endogenous growth hormone.

In particular, certain spiro compounds are disclosed in U.S. Pat. No. 5,536,716, PCT Patent Publication WO 94/13696 and *Proc. Natl. Acad. Sci. USA* 92, 7001–7005 (July 1995) as being non-peptidal growth hormone secretagogues. These compounds have the ability to stimulate the release of natural or endogenous growth hormone and thus may be used to treat conditions which require the stimulation of growth hormone production or secretion such as in humans with a deficiency of natural growth hormone or in animals used for food or wool production where the stimulation of growth hormone will result in a larger, more productive animal.

Among the preferred compounds disclosed therein is spiro[3H-indole-3,4'-piperdin]-1'-yl)carbonyl]-2-(phenylmethyl-oxy)ethyl]-2-amino-2-methylpropanamide which has the structure:

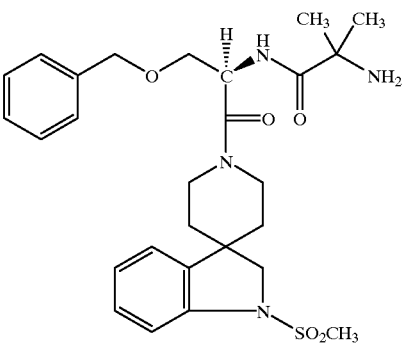

U.S. Pat. No. 5,536,716 and PCT Patent Publication WO 94/13696 disclose methods for preparing this compound (see Examples 18, 19 and 55). However, the synthesis of the compound was accomplished by using the very expensive amino acid coupling agent EDC ($1100/kg); the use of numerous equivalents of trifluoroacetic acid as the catalyst for the BOC group deprotections; extensive chromatographic purifications; and resulted in "gumming" of the final product. PCT Patent Publication WO 97/15573 also discloses methods for preparing this compound.

The advantages of the present invention include: manufacturing flexibility through a convergent route; synthesis of the dipeptide side-chain in high yield and high enantiomeric excess; avoidance of a large number of steps (i.e. coupling/deprotection sequences) in the presence of the spiroindoline; a high yielding non-isolation process; decreased expense through the use of DCC [$40/kg] instead of EDC [$1100/kg]; diminished environmental impact through the use of methanesulfonic acid instead of trifluoroacetic acid as the catalyst (as well as lesser equivalents of catalyst) in the deprotections; and ease of isolation of the final product.

SUMMARY OF THE INVENTION

The instant invention is directed to a novel convergent process for the preparation of the compound N-[1(R)-[(1,2-dihydro-1-methanesulfonyl-spiro[3H-indole-3,4'-piperdin]-1'-yl)carbonyl]-2-(phenylmethyl-oxy)ethyl]-2-amino-2-methyl-propanamide which has the structure:

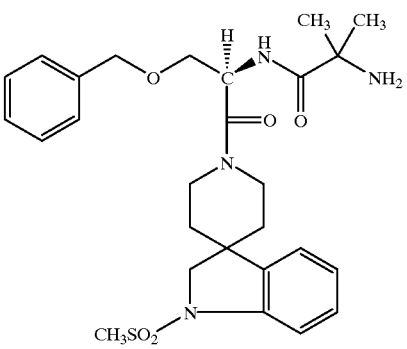

and salts thereof, in particular, the methanesulfonate salt. This compound has the ability to stimulate the release of natural or endogenous growth hormone and may be used to treat conditions which require the stimulation of growth hormone production or secretion such as in humans with a deficiency of natural growth hormone or in animals used for food or wool production where the stimulation of growth hormone will result in a larger, more productive animal.

DESCRIPTION OF THE INVENTION

The present invention is directed to a novel convergent process for the preparation of the compound N-[1(R)-[(1,2-dihydro-1-methanesulfonyl-spiro[3H-indole-3,4'-piperdin]-1'-yl)carbonyl]-2-(phenylmethyl-oxy)ethyl]-2-amino-2-methyl-propanamide which has the structure:

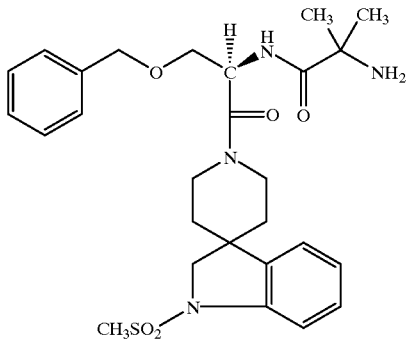

and salts thereof, in particular, the methanesulfonate salt.

The instant process provides the desired compound from readily available inexpensive and environmentally acceptable starting materials reagents and solvents. The process does not require the use any chromatographic purifications, and it is possible to produce the final product from the intermediate spiroindoline sulfonamide without isolation of any of the intermediates.

The individual processes within the general process are summarized as follows:

SCHEME I

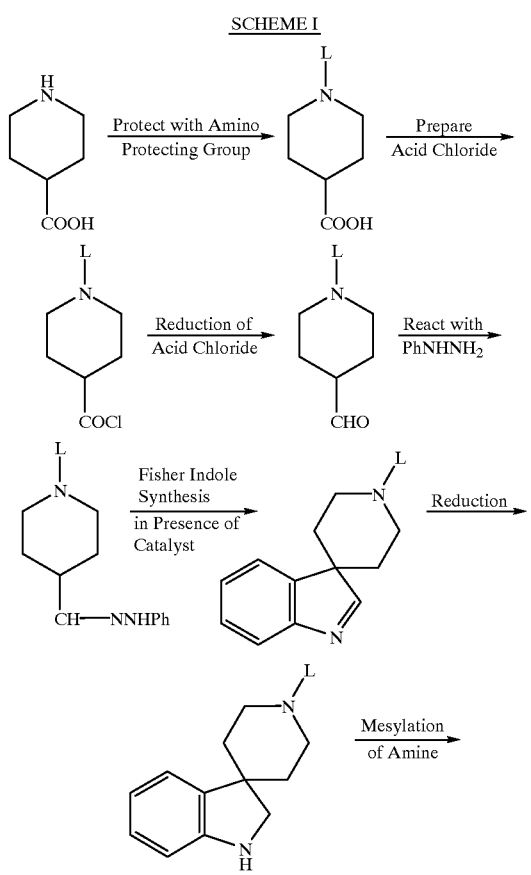

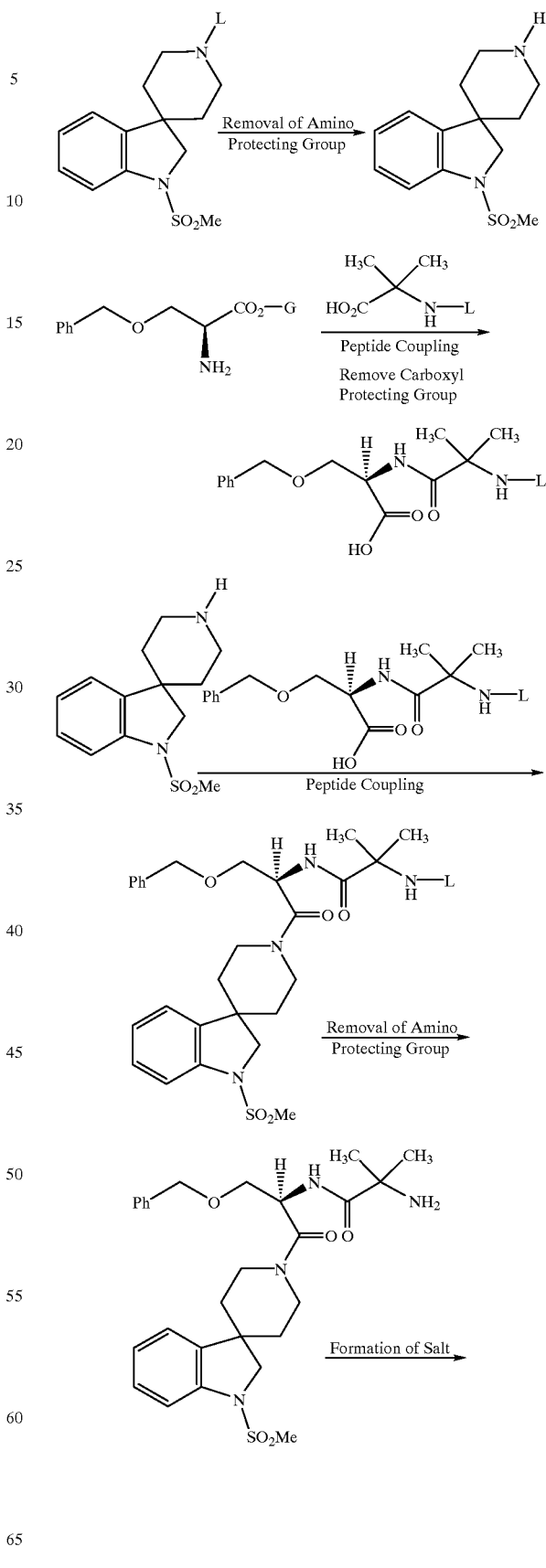

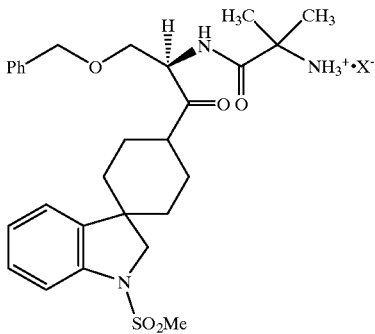

(wherein G is an appropriate carboxyl protecting group, L is an appropriate amino protecting group and X⁻ is an appropriate counterion).

Within this general process, a first process concerns the preparation of a compound of formula I:

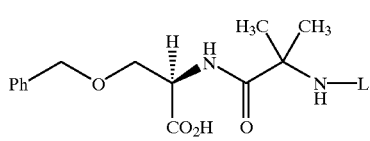

wherein L is an amino protecting group, by coupling an amino acid of the formula:

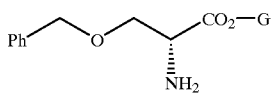

wherein G is a carboxyl protecting group, with a compound of the formula:

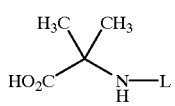

wherein L is an amino protecting group, in the presence of an acid activating agent in an inert solvent in the presence of a catalytic agent, followed by removal of the carboxyl protecting group G to give the compound of formula I.

Acid activating agents suitable for this process include: DCC, EDC, ECAC and BOP, in which the preferred acid activating agent is DCC (N,N'-dicyclohexylcarbodiimide).

Catalytic agents suitable for this process include: HOBT, HONB, and the like in which a preferred catalytic agent is HOBT (hydroxybenzotriazole).

Inert solvents appropriate for this processes include: acetonitrile; iso-propyl acetate; ethyl acetate; propionitrile; water; chlorinated hydrocarbons such as dichloromethane, chloroform, carbon tetrachloride, dichloroethane, chlorobenzene, ortho-dichlorobenzene; benzene; toluene; xylenes; and the like; and mixtures thereof, in which the preferred solvent is either acetonitrile or isopropyl acetate and water.

The preferred reaction temperature range is between −40 and 150° C., and the most preferred range is between 20 and 35° C.

Suitable carboxyl protecting groups include: methyl, allyl, ethyl, isopropyl, benzyl, and the like, in which the preferred one is methyl.

Removal of the carboxyl protecting group may be effected by methods well known in the art. For example, hydrolysis of the methyl ester may be achieved with lithium hydroxide in a solution of toluene and water at a temperature of between about 0 and about 10° C., preferably about 4–5° C. Optionally, the enantiomeric purity of the dipeptide may be upgraded by formation and crystalization of the dicyclohexyl amine salt.

Suitable amino protecting groups include: benzyl, benzyloxymethyl, benzyloxycarbonyl (carbobenzyloxy), benzylsulfonyl, 2-bromo-ethyloxycarbonyl, t-butoxy-carbonyl, 2-chloro-benzyloxy-carbonyl, 2-chloroethyloxycarbonyl, di-t-amyloxycarbonyl, 9-fluoroenylmethyloxycarbonyl, isopropoxycarbonyl, 4-methoxy-benzyloxycarbonyl, 4-nitrobenzyloxycarbonyl, 2-nitrophenyl-sulfonyl, phthaloyl, 2,2,2-trichloro-t-butyloxycarbonyl, trifluoroacetyl, triphenylmethane, allyloxycarbonyl, and vinyloxycarbonyl groups, and the like, in which the preferred ones include benzyloxycarbonyl (carbobenzyloxy), t-butoxy-carbonyl groups, and in which the most preferred one is the t-butoxy-carbonyl group.

In the interest of efficiency, it is preferred that this coupling be conducted in situ without isolation of the compound of formula I following its preparation by the aforementioned process.

Within this general process, a second process concerns the preparation of a compound of formula II:

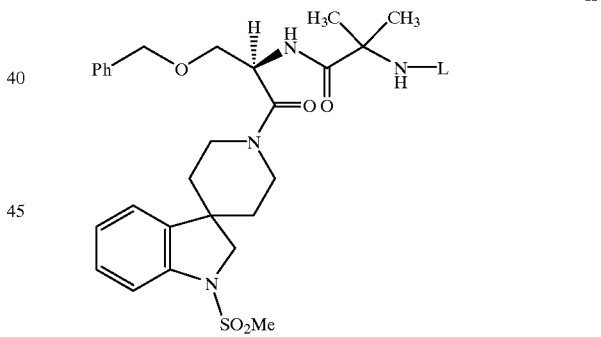

wherein L is an amino protecting group, by coupling an amino acid of the formula:

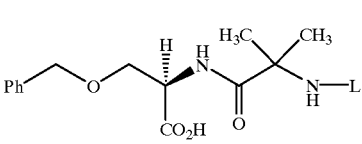

wherein L is an amino protecting group, with a compound of the formula:

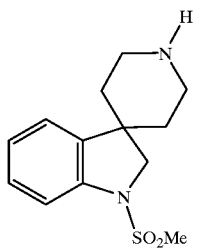

in the presence of an acid activating agent in an inert solvent in the presence of a catalytic agent, to give the compound of formula II.

Acid activating agents suitable for this process include: DCC, EDC, ECAC and BOP, in which the preferred acid activating agent is DCC (N,N'-dicyclohexylcarbodiimide).

Catalytic agents suitable for this process include: HOBT, HONB, and the like in which a preferred catalytic agent is HOBT (hydroxybenzotriazole) or HONB (N-hydroxy-5-norbornene-2,3-dicarboximide).

Inert solvents appropriate for this processes include: acetonitrile; isopropyl acetate; ethyl acetate; propionitrile; water; chlorinated hydrocarbons such as dichloromethane, chloroform, carbon tetrachloride, dichloroethane, chlorobenzene, ortho-dichlorobenzene; benzene; toluene; xylenes; and the like; and mixtures thereof. When the catalytic agent is HOBT, the preferred solvent is acetonitrile. When the catalytic agent is HONB, the preferred solvent is isopropyl acetate:water.

The preferred reaction temperature range is between −40 and 150° C. When the catalytic agent is HOBT, the most preferred range is between about −20 and about −35° C., and the even more preferred temperature is about −25° C. When the catalytic agent is HONB, the most preferred range is between about −10 and about 15° C., and the even more preferred temperature range is between about 0 and 5° C.

Suitable amino protecting groups include: benzyl, benzyloxymethyl, benzyloxycarbonyl (carbobenzyloxy), benzylsulfonyl, 2-bromo-ethyloxycarbonyl, t-butoxy-carbonyl, 2-chloro-benzyloxy-carbonyl, 2-chloroethyloxycarbonyl, di-t-amyloxycarbonyl, 9-fluoroenylmethyloxycarbonyl, isopropoxycarbonyl, 4-methoxy-benzyloxycarbonyl, 4-nitrobenzyloxycarbonyl, 2-nitrophenyl-sulfonyl, phthaloyl, 2,2,2-trichloro-t-butyloxycarbonyl, trifluoroacetyl, triphenylmethane, allyloxycarbonyl, and vinyloxycarbonyl groups, and the like, in which the preferred ones include benzyloxycarbonyl (carbobenzyloxy), t-butoxy-carbonyl groups, and in which the most preferred one is the t-butoxy-carbonyl group.

In the interest of efficiency, it is preferred that this coupling be conducted in situ without isolation of the compound of formula II following its preparation by the aforementioned process. Alternatively, the compound of formula II may be isolated as a discrete intermediate.

Within this general process, a third process concerns the preparation of a compound of formula III, or a pharmaceutically acceptable salt thereof:

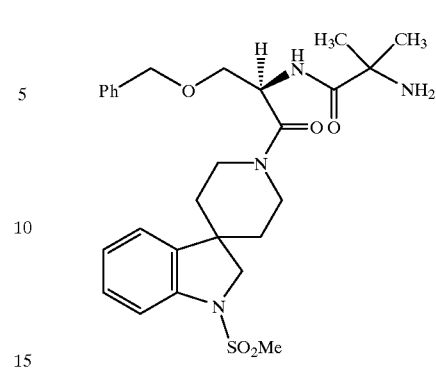

which comprises reacting a compound of the formula II:

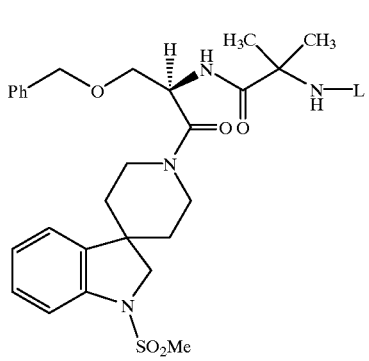

wherein L is an amino protecting group, with an amino deprotecting agent to give the compound of formula III.

Suitable amino protecting groups include: benzyl, benzyloxymethyl, benzyloxycarbonyl (carbobenzyloxy), benzylsulfonyl, 2-bromo-ethyloxycarbonyl, t-butoxy-carbonyl, 2-chloro-benzyloxy-carbonyl, 2-chloroethyloxycarbonyl, di-t-amyloxycarbonyl, 9-fluoroenylmethyloxycarbonyl, isopropoxycarbonyl, 4-methoxy-benzyloxycarbonyl, 4-nitrobenzyloxycarbonyl, 2-nitrophenyl-sulfonyl, phthaloyl, 2,2,2-trichloro-t-butyloxycarbonyl, trifluoroacetyl, triphenylmethane, allyloxycarbonyl, and vinyloxycarbonyl groups, and the like, in which the preferred ones include benzyloxycarbonyl (carbobenzyloxy), t-butoxy-carbonyl groups, and in which the most preferred one is the t-butoxy-carbonyl group.

In this process, the removal of the amino protecting group may be accomplished by use of an appropriate catalytic agent. Removal of a t-butoxycarbonyl protecting group may be carried out in a solvent such as methanol, ethanol, methylene chloride, ethyl acetate, or iso-propyl acetate, with a strong acid. Such strong acids include methanesulfonic acid, trifluoroacetic acid, hydrochloric acid, hydrogen chloride gas, hydrogen bromide; hydrogen iodide; trifluoromethane-sulfonic acid; camphorsulfonic acid; sulfuric acid; phosphoric acid; and an arylsulfonic acid, such as benzenesulfonic acid, p-toluenesulfonic acid, and p-chlorobenzene-sulfonic acid. Preferred catalytic agents include: trifluoroacetic acid; methanesulfonic acid; camphorsulfonic acid; benzenesulfonic acid, p-toluenesulfonic acid; and p-chlorobenzene-sulfonic acid. The most preferred catalytic agent is methanesulfonic acid. It is preferred that compound of formula III is isolated in the form of the methanesulfonate salt. The preferred solvent is methanol or ethanol, and the most preferred solvent is ethanol.

The preferred reaction temperature range is between −40 and 150° C., and the most preferred range is between 10 and 40° C.

Removal of a benzyloxycarbonyl (carbobenzyloxy) group may be achieved by a number of methods, for example, catalytic hydrogenation with hydrogen in the presence of a noble metal or its oxide such as palladium on activated carbon in a protic solvent such as ethanol. In cases where catalytic hydrogenation is contraindicated by the presence of other potentially reactive functionality, the removal of benzyloxycarbonyl (carbobenzyloxy) group may also be achieved by treatment with a solution of hydrogen bromide in acetic acid, or by treatment with a mixture of TFA and dimethylsulfide.

In the interest of efficiency, it is preferred that this acid-catalyzed deprotection be conducted in situ without isolation of the compound of formula III following its preparation by the aforementioned process.

Within this general process, a fourth process concerns the preparation of a pharmaceutically acceptable salt of a compound of formula III, in particular, the methanesulfonate salt, i.e. a compound of formula IV:

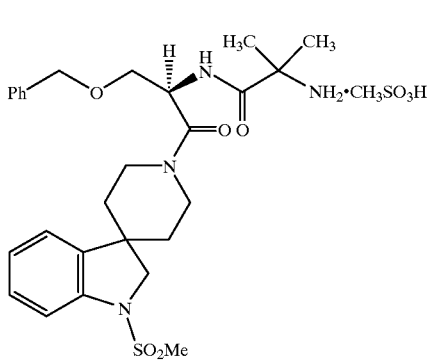

IV which comprises reacting a compound of the formula III:

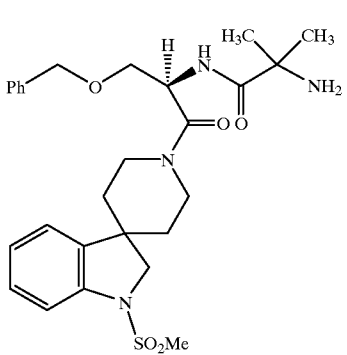

III with an acid, preferably methanesulfonic acid, to give the compound of formula IV.

It is preferred that compound of formula IV is isolated in the form of the methanesulfonate salt. The preferred solvent comprises ethyl acetate and ethanol, and the most preferrred solvent is a mixture of ethyl acetate and ethanol.

In the interest of efficiency, it is preferred that the formation of the salt be conducted in situ without isolation of the compound of formula V following its preparation by the aforementioned process.

In a preferred embodiment of the present invention, the individual processes within the general process are outlined as follows:

SCHEME II:

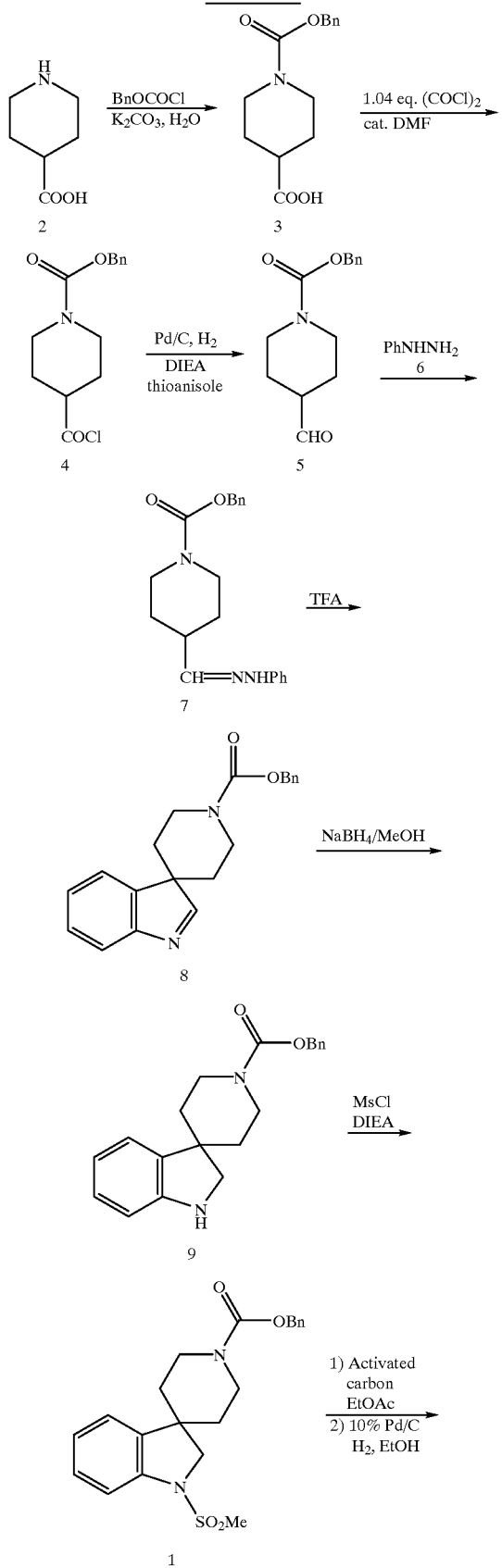

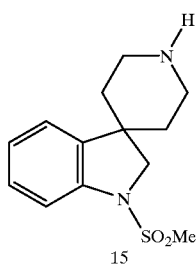

SCHEME III

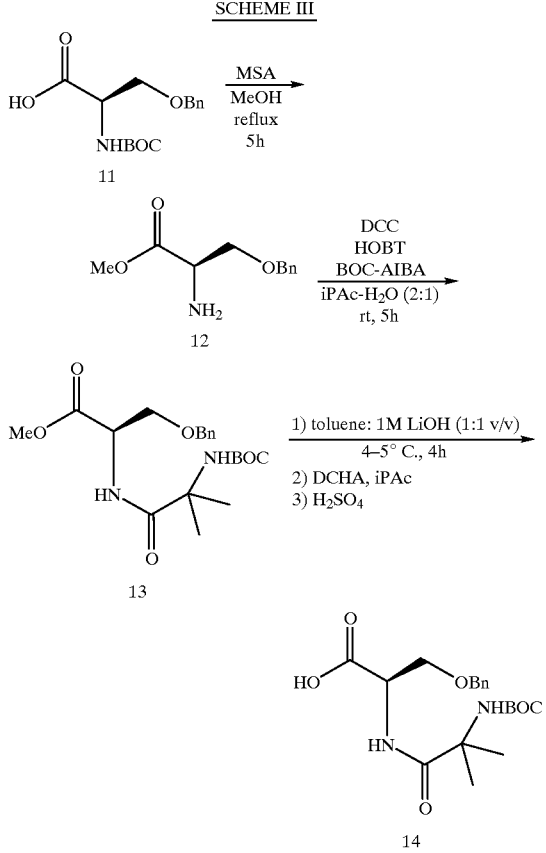

The N-BOC-O-Benzyl-D-Serine 11 was treated with methane sulfonic acid in methanol at 65° C. for ca. 5 hours to affect simultaneous BOC deprotection and methyl ester formation in 90–95% yield. The success of this reaction depended on a careful workup procedure that avoided hydrolysis of the methyl ester (12). To that end, the methanolic solution of 2 was solvent switched to iPAc (levels of residual MeOH of <1% v/v are essential). A 15% aqueous NaCl solution was added and the biphasic mixture was cooled to 0° C. A solution of NaOH (2 N) was added slowly to pH 9, at 0–4° C., and the pH was carefully adjusted to 10.2 with 0.5 N NaOH. A lower pH resulted in substantial losses of 12 in the aqueous layer, while at pH 11, substantial hydrolysis of the methyl ester was observed.

Coupling of 12 with N-BOC-amino isobutyric acid was accomplished in iPAC-H$_2$O (2:1 v/v) in the presence of DCC (1.1 eq) and HOBT (0.05 eq), to afford 13 in 98% crude yield.

The crude methyl ester 13 was hydrolyzed in high yield (95–97%) with minimal epimerization at the serine chiral center (ca. ≦2%). The reproducibility of this reaction was initially tenuous, however, a reliable procedure was developed. Intermediate 13 was dissolved in toluene:H$_2$O (2:1 v/v), then cooled to 4° C. and treated with 2 N LiOH (2.5 eq). The aqueous layer, containing the Li salt of 14, was separated; iPAc was added and the pH was adjusted to ca. 1 with 1.5 N HCl. The enantiometric purity of 14 was upgraded to >99.5% ee developed by the following procedure: 1) addition of DCHA in iPAC at 65° C.; 2) aging the resulting thick slurry at that temperature for 4–5 hours; and 3) aging at 25° C. for 10 hours followed by filtration. The enantiomerically pure free acid, 14, was obtained in high overall yield (ca. 93%) by partitioning the DCHA salt in iPAc-1 M H$_2$SO$_4$ (aqueous) followed by separation of the layers, volume adjustment of the organic layer (ca. 3 volumes), and addition of heptane (ca. 9 volumes).

SCHEME IV

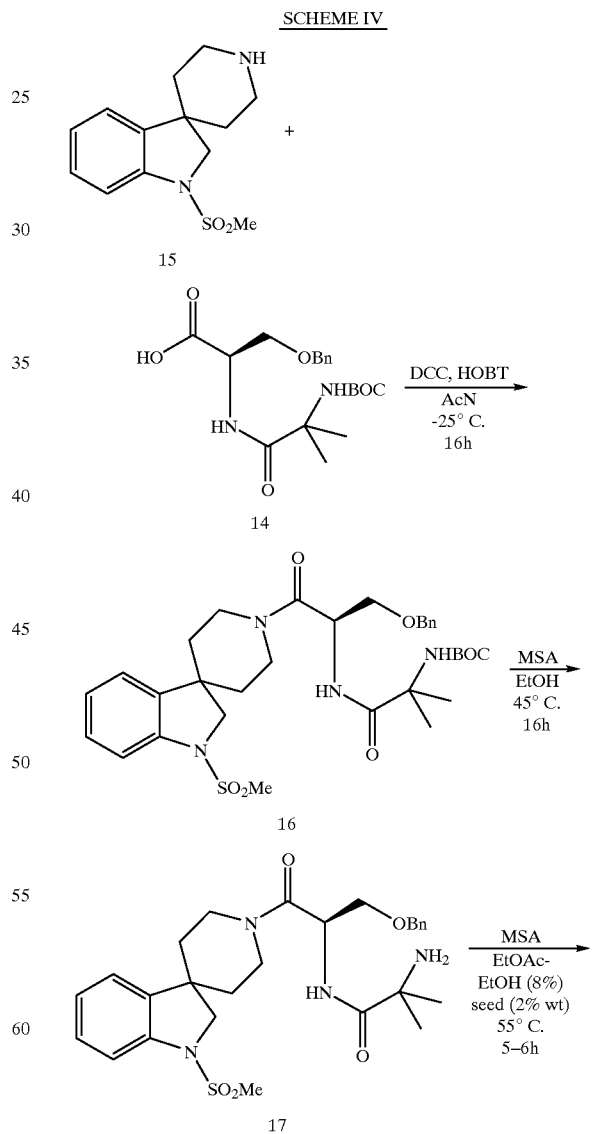

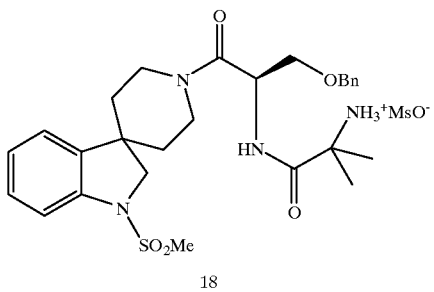

18

Reaction of 15 with 14 in CH$_3$CN (1.1 eq DCC; 0.2 eq HOBT) at −25° C. produced 0.4% of the L-isomer (specification: <0.5%) of 16 and eventually the final product 18. Similarly, reaction of 15 with14 in 2:1 iPAc:H$_{20}$ (1.1 eq DCC; 0.2 eq HONB) at 0° C. produced very little of the L-isomer of 16.

The ethyl acetate solution of the free base 17 is concentrated to low bulk in vacuo and is azeotroped dry (KF <500 mgml$^{-1}$) by "feeding and bleeding" 2× batch volumes of 90/10, ethyl acetate/ethanol followed by 2× batch volumes of ethyl acetate. The resulting dry, slightly hazy solution of the free base 17 in ethyl acetate is treated with Darco G-60 (25 weight %) at room temperature for about 10 hours. Removal of the Darco by filtration with a filtration agent gives the free base 17.

Formation of the methanesulfonic acid salt 18 from 17 is carried out in EtOAc with 1.1 eq of MsOH at about 50° C. The free base 17 is treated with 8 volume % of EtOH and 1 eq of H$_2$O and heated to 55° C. until complete dissolution. Cooling to ambient temperature and stirring the resulting slurry for 4 hours gives crystalline material of 18 designated as crystal Form II [solubility in IPA=12 mg/mL].

The conversion of Form II to Form I is accomplished where the salt is formed in EtOAc-EtOH as above, but instead of cooling the initial solution of the salt (at 55° C.) to ambient temperature, it is cooled to 45° C. Crystals should start appearing at that temperature and the slurry should become thicker with time. The temperature is then raised to 51° C. and the slurry is aged overnight. Complete conversion to Form I of 18 should be expected.

Preferably, the conversion of Form II to Form I is achieved by adding seed crystals of Form I to a solution of the free base in EtOAc-EtOH at 50–55° C. followed by aging. Accordingly, the free base 17 may be treated with 1.1 equivs. of methanesulfonic acid in 8% ethanol in ethyl acetate at 50–55° C. The batch is then seeded with approximately 2% by weight of Form I of the methanesulfonate salt 18, and then aged at 55° C. overnight. The batch is cooled to room temperature and aged for approximately 2–3 hours. The product is isolated by filtration at room temperature under a nitrogen atmosphere, dried at 35° C. in vacuo and sieved to give the methanesulfonate salt 18.

The methanesulfonic acid salt 18 may also be formed by alternating the stepwise addition of MsOH (1.1 eq) and seed crystals of Form I to a solution of the free base in EtOAc-EtOH at about 50° C., wherein the order of addition of the MsOH and the seed is not critical.

Detailed solubility studies showed that no thermodynamic enrichment was possible during the isolation of 16 (EtOH/ heptane) or 18 (EtOAc:EtOH, 92:8). In an attempt to prevent epimerization, a number of reaction parameters were examined; these included temperature, order of addition of the reagents, solvent, amount of HOBT, and coupling reagent. The results are summarized in Table 1.

TABLE I

| solvent | 25° C. | 0° C. | −7° C. | −25° C. | 0° C./EDC |
|---|---|---|---|---|---|
| iPAC/H$_2$O | 8% L | 3% L | — | — | 10% L |
| AcN | 4% L | 1% L | 0.8–1% L | 0.4% L | — |

In the optimal reaction conditions, spiroindoline 15 and dipeptide 14 were dissolved in 13 volumes of acetonitrile and HOBT was added (1.1 eq). Alternatively, HONB (N-hydroxy-5-norbornene-2,3-dicarboximide) may be employed in place of HOBT. The resulting homogenous mixture was treated with DCC in acetonitrile at −25° C. overnight. [Note: This order of addition is crucial since 15 and HOBT form an insoluble complex throughout the reaction which makes stirring difficult and might be responsible for some initial irreproducibility in the results.] After workup, the dipeptide-BOC, 16, was isolated and carried to the final product to afford the final compound in ca. 70% overall yield from 11 in 99.9% purity and 99.2% ee.

Throughout the instant application, the following abbreviations are used with the following meanings:

| Bu | butyl |
|---|---|
| Bn | benzyl |
| BOC, Boc | t-butyloxycarbonyl |
| BOP | Benzotriazol-1-yloxy tris(dimethylamino)-phosphonium hexafluorophosphate |
| calc. | calculated |
| CBZ, Cbz | Benzyloxycarbonyl |
| DCC | N,N'-Dicyclohexylcarbodiimide |
| DIEA | Di-isopropylethylamine |
| DMF | N,N-dimethylformamide |
| DMAP | 4-Dimethylaminopyridine |
| EDC | 1-(3-dimethylaminopropyl)-3-ethylcarbodiimide hydrochloride |
| EDAC | Ethyl-3-(3-dimethylamino)-propylcarbodiimide |
| EI-MS | Electron ion-mass spectroscopy |
| Et | ethyl |
| eq. | equivalent(s) |
| FAB-MS | Fast atom bombardment-mass spectroscopy |
| h, hr. | hours |
| HOBT, HOBt | Hydroxybenzotriazole |
| HPLC | High pressure liquid chromatography |
| iPrOAc | iso-Propyl acetate |
| KHMDS | Potassium bis(trimethylsilyl)amide |
| LAH | Lithium aluminum hydride |
| LHMDS | Lithium bis(trimethylsilyl)amide |
| Me | methyl |
| MF | Molecular formula |
| MHz | Megahertz |
| MPLC | Medium pressure liquid chromatography |
| MsOH | Methane sulfonic acid |
| NMM | N-Methylmorpholine |
| NMR | Nuclear Magnetic Resonance |
| Ph | phenyl |
| Pr | propyl |
| prep. | prepared |
| TFA | Trifluoroacetic acid |
| THF | Tetrahydrofuran |
| TLC | Thin layer chromatography |
| TMS | Tetramethylsilane |

In the above structural formula and throughout the instant specification, the following terms have the indicated meanings:

The phrase "peptide coupling reaction" as used herein is intended to mean the coupling of a carboxylic acid with an amine using an acid activating agent such as EDC, DCC, and BOP in an inert solvent in the presence of a catalyst such as HOBT. Inert solvents appropriate for such couplings include: acetonitrile; iso-propyl acetate; ethyl acetate; propionitrile; water; chlorinated hydrocarbons such as dichloromethane, chloroform, carbon tetrachloride, dichloroethane, chlorobenzene, orthodichlorobenzene; benzene; toluene; xylenes; and combinations thereof; and the like.

The variable "L" and the term "amino protecting group" is intended to indicate the presence of an appropriate protecting group for amino, such as those described in Greene, T. W., Wuts, P. G. M. Protective Groups in Organic Synthesis, 2nd ed., John Wiley & Sons, Inc., New York, 1991. An appropriate protecting group will be able to withstand the reaction conditions of intermediate processes, prior to being removed when desired. The amino protecting group is independently selected for each process within the entire processes.

Suitable amino protecting groups include: benzyl, benzyloxymethyl, benzyloxycarbonyl (carbobenzyloxy), benzylsulfonyl, 2-bromo-ethyloxycarbonyl, t-butoxycarbonyl, 2-chloro-benzyloxy-carbonyl, 2-chloroethyloxycarbonyl, di-t-amyloxycarbonyl, 9-fluoroenylmethyloxycarbonyl, isopropoxycarbonyl, 4-methoxy-benzyloxycarbonyl, 4-nitrobenzyloxycarbonyl, 2-nitrophenyl-sulfonyl, phthaloyl, 2,2,2-trichloro-t-butyloxycarbonyl, trifluoroacetyl, triphenylmethane, and vinyloxycarbonyl groups, and the like, in which the preferred ones include benzyloxycarbonyl (carbobenzyloxy), t-butoxy-carbonyl groups, and in which the most preferred one is the t-butoxy-carbonyl group.

The removal of the amino protecting group may be accomplished by use of an appropriate catalytic agent. Removal of a t-butoxycarbonyl protecting group may be carried out in a solvent such as methanol, ethanol, methylene chloride, ethyl acetate, or iso-propyl acetate, with a strong acid. Such strong acids include methanesulfonic acid, trifluoroacetic acid, hydrochloric acid, hydrogen chloride gas, hydrogen bromide; hydrogen iodide; trifluoromethanesulfonic acid; camphorsulfonic acid; sulfuric acid; phosphoric acid; and arylsulfonic acids, such as benzenesulfonic acid, p-toluenesulfonic acid, and p-chlorobenzene-sulfonic acid. Preferred catalytic agents include: trifluoroacetic acid; methanesulfonic acid; camphorsulfonic acid; benzenesulfonic acid, p-toluenesulfonic acid; and p-chlorobenzene-sulfonic acid. The most preferred catalytic agent is methanesulfonic acid. The preferred solvent is methanol or ethanol.

Removal of a benzyloxycarbonyl (carbobenzyloxy) protecting group may be achieved by a number of methods, for example, catalytic hydrogenation with hydrogen in the presence of a noble metal or its oxide such as palladium on activated carbon in a protic solvent such as ethanol. In cases where catalytic hydrogenation is contraindicated by the presence of other potentially reactive functionality, the removal of benzyloxycarbonyl (carbobenzyloxy) group may also be achieved by treatment with a solution of hydrogen bromide in acetic acid, or by treatment with a mixture of TFA and dimethylsulfide.

The amine compounds employed as starting materials for the process of the present invention may be present as their acid salts, such as the salts derived from using inorganic and organic acids. Examples of such acids are hydrochloric, nitric, sulfuric, phosphoric, formic, acetic, trifluoroacetic, propionic, maleic, succinic, malonic, methane sulfonic and the like. Similarly the compounds produced by the processes of the instant invention may be isolated in the form of their pharmaceutically acceptable acid salts. In addition, certain compounds containing an acidic function such as a carboxy can be in the form of their inorganic salt in which the counterion can be selected from sodium, potassium, lithium, calcium, magnesium and the like, as well as from organic bases.

The preparation of compounds with the process of the present invention may be carried out in sequential or convergent synthetic routes. It is noted that in some cases the order of carrying out the foregoing reaction schemes may be varied to facilitate the reaction or to avoid unwanted reaction products. In general, the process of the present invention is conducted in a sequential manner as presented herein.

Many of the starting materials are either commercially available or known in the literature and others can be prepared following literature methods described for analogous compounds. The skills required in carrying out the reaction and purification of the resulting reaction products are known to those in the art. Purification procedures include crystallization, normal phase or reverse phase chromatography.

The following examples are provided for the purpose of further illustration only and are not intended to be limitations on the disclosed invention.

EXAMPLE 1

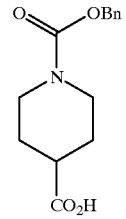

3

| Isonipecotic acid-N-benzyl carbamate (3) | |
|---|---|
| Materials: | |
| sonipecotic acid (2) T.C.I. | 4.02 kg (31.1 mol) |
| Benzyl chloroformate (Schweitzerhall) | 6.91 kg (40.5 mol) |
| $K_2CO_3$ | 10.1 kg (72.9 mol) |
| Water | 40.2 L |

Isonipecotic acid (2) and $K_2CO_3$ were dissolved in 40.2 L of water in a 100 L 4 neck flask with mechanical stirring under $N_2$ and the solution was cooled to 10° C. Benzyl chloroformate was added, maintaining the temperature between 9 and 14° C., and the mixture was warmed up to 22° C. after the addition was complete and aged for 58 h. The addition was completed in 4 h at which point the pH was 9.0. After aging for 58 h there was no change in the pH.

The reaction mixture was transferred to a 200 L extractor and washed with 3×13 kg (15 L) of IPAC and 1×12 L of EtOAc. The aqueous layer was extracted with 8 L of toluene. After the washes the benzyl alcohol content was reduced from 3.8% to 1.4% by HPLC analysis. HPLC analytical: Dupont Zorbax 25 cm RXC8 column with 1.5 mL/min flow and detection at 254 nm; isocratic mixture with 35% MeCN, 65% of 0.1% aqueous $H_3PO_4$; retention times: 3=6.9 min, benzyl alcohol=3.3 min, toluene=17.3 min.

The aqueous phase was acidified with 37% aqueous HCl to pH 1.8. Carbon dioxide was evolved during the addition of HCl, but gas evolution was easily controlled. The addition of HCl took <1 h and required 10 L of conc. HCl. The aqueous phase was extracted with 3×6.6 L of toluene. The toluene extracts were dried with 2 kg of sodium sulfate and filtered through a pad of Solka-floc™. The combined filtrates weighed 17.8 kg. The crude yield of carbamate 3 was 7.89 kg (97%) (as obtained by evaporation of weighed aliquots of the filtrates to dryness). The filtrates were transferred through a 10 μ inline filter to a 100 L flask. The extracts were concentrated at 10 mbar at <25° C. to a volume of 18 L. The final concentration of carbamate 3 was 440 g/L. The concentration of the toluene filtrate served to azeotropically remove final traces of water (final KF=170mg/L). The product was 99.1 area % pure with 0.9 area % benzyl alcohol as the only impurity.

EXAMPLE 2

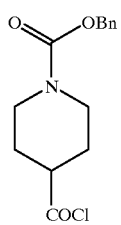

4

Isonipecotic acid chloride-N-benzyl carbamate (4)

Materials:

| | |
|---|---|
| Isonipecotic acid N-benzyl carbamate (3) in toluene. (MW = 263.30) | 7.89 kg (30.0 mol) in 17.9 L |
| Oxalyl chloride (MW = 126.93) | 3.94 kg (31.0 mol) |
| DMF (MW = 73.10) | 10 mL |
| Toluene | 12 L |

To the toluene solution of benzyl carbamate 3 from the preceding step was added 5 mL of DMF and 10 L of toluene. The oxalyl chloride was added over a period of 20 min. The reaction mixture was aged for 16 h at 18° C. under a slow stream of nitrogen. HPLC analysis of the reaction mixture showed that 1.3% of the carboxylic acid 3 still remained unreacted. The reaction mixture was warmed to 26° C., and 5 mL of DMF were added. The mixture was aged for 2.5 h.

A 1.0 mL aliquot of the reaction mixture was quenched with 5.0 mL of tert-butylamine and analyzed after evaporation by HPLC: 25 cm Dupont Zorbax RXC8 column at 50° C. with 1 mL/min flow and detection at 220 nm; isocratic 42% MeCN, 58% of 0.1% aqueous $H_3PO_4$. This method showed that <0.05% of the acid 3 remained (as judged by A) and showed >3 area % B (>1 mol % $(COCl)_2$).

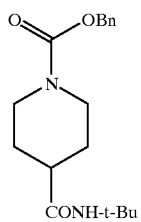

A

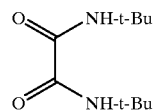

B

The mixture was concentrated at 10 mbar and a temperature of 20–25° C. until 5 L of solvent had been removed.

The typical HPLC profile of concentrated toluene solution after t-BuNH$_2$ quench described above is as follows:

| Retention time (min) | Area % | Identity |
|---|---|---|
| 2.1 | <0.5% | carboxylic acid 3 |
| 7.8 | <0.5% | benzyl chloride |
| 11.0 | >99% | Cbz-t-butylcarboxamide A |
| 12.1 | NA | toluene |
| 12.7 | <0.5% | ditert-butyloxamide B |

EXAMPLE 3

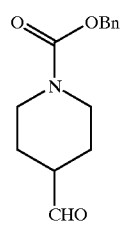

5

Piperidine-4-carboxaldehyde-1-benzyl carbamate (5)

Materials:

| | |
|---|---|
| Isonipecotic acid chloride N-benzyl carbamate (4) in toluene (MW = 281.74) | 3.38 kg (12.0 mol) in 5.54 kg |
| DIEA (KF = 18 mg/L) | 1.55 kg (15.0 mol) |
| 10% Pd/C (KF < 20 mg/g) | 101 g |
| thioanisole (MW = 124.21, d = 1.058) | 0.56 g |

The DIEA and thioanisole were added to the solution of (4) in toluene from the previous step and the catalyst was suspended in this mixture. The mixture was immediately placed into the 5 gal autoclave and hydrogenated at 20° C. and 40 psi of $H_2$. After 18 h the reaction had taken up 70% the theoretical amount of hydrogen and HPLC analysis of an aliquot that was quenched with tert-butylamine indicated that 14.2 area % of acid chloride 2 remained. HPLC conditions same as above. Retention time: 5=8.1 min.

A second charge of catalyst (101 g) and thioanisole (0.54 g) were added as a slurry in 1375 mL toluene to the hydrogenator. After 23 h HPLC analysis of an aliquot that was quenched with tert-butylamine indicated that 1.8 area % of acid chloride 2 remained. The mixture was purged with nitrogen and the catalyst-and precipitated DIEA•HCl were it removed by filtration through Solka-floc™. The filter cake was washed with 10 L of toluene. The filtrates were transferred through a 10 μ inline filter to a 50 L extractor and washed with 2×7.2 L of 1 M aqueous HCl and 2×7.2 L of water. The mixture was concentrated at 10 mbar and a temperature of 25–30° C. until 5 L of residue remained.

| Retention time (min) | Area % | Identity |
|---|---|---|
| 2.1 | <2 | carboxylic acid 3 |
| 6.6 | <1 | dimer 21 |
| 8.1 | >95 | aldehyde 5 |

The assay yield of aldehyde 3 was 94% by HPLC analysis.

EXAMPLE 4

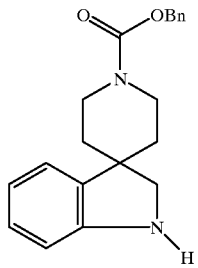

CBZ-Spiroindoline (9)

Materials:

| Piperidine-4-carboxaldehyde-1-benzyl toluene solution | 1.71 kg (6.89 mol) carbamate (5) in 21.4 kg |
|---|---|
| Phenylhydrazine | 900 mL, 981 g (9.15 mol) |
| Trifluoroacetic acid (TFA) | 2.20 L, 3.26 kg (28.6 mol) |
| NaBH$_4$ | 300 g, (7.93 mol) |
| Toluene | 34.4 kg |
| MeCN | 7.0 L |
| MeOH | 7.0 L |

The crude aldehyde 5 solution from the previous step was transferred through a 10 μ inline filter to a 100 L reactor equipped with Teflon coated copper coils for cooling or heating and a mechanical stirrer. Toluene (34.4 kg) and MeCN (7 L) were added, and the resulting solution was cooled to 0° C. Phenylhydrazine was added in portions and the temperature was maintained at −1 to 3° C. while nitrogen was continuously bubbled through the reaction mixture.

The phenylhydrazine was added until TLC and HPLC analysis indicated complete consumption of the aldehyde 5 and the appearance of a slight excess (<5%) of phenylhydrazine. TLC conditions: Silica, E. Merck Kieselgel G60 F254 0.25 mm; diethyl ether/pentane (4/1); and developing agent 0.5% ceric sulfate, 14% ammonium molybdate in 10% aqueous sulfuric acid then heat; Rf. aldehyde 5=0.52, phenylhydrazone 7=0.61, phenylhydrazine 6=0.21. HPLC conditions: 25 cm Dupont Zorbax RXC8 column at 30° C. with 1.0 mL/min flow and detection at 254 nm; gradient schedule:

| Time (min) | acetonitrile:water |
|---|---|
| 0 | 57:43 |
| 10 | 65:35 |
| 15 | 75:25 |
| 18 | 75:25 | retention times: phenylhydrazine 6=4.5 min, toluene=7.2 min, phenylhydrazone 7=11.4 min.

The reaction mixture was aged for 30 min at 0–2° C., and TFA was added maintaining the temperature between 2 and 7° C. The reaction mixture was warmed to 50° C. over 30 min, and maintained for 17 h. The nitrogen sparge through the reaction mixture was stopped and a slow stream of nitrogen was maintained over the reaction mixture. During the first hour at 5° C. the color gradually darkened to a deep green, and a relatively small amount of a white crystalline precipitate (ammonium trifluoroacetate) formed. After 17 h HPLC analysis (same conditions as above) indicated that the reaction mixture contained 91.6 area % indolenine 8 and 1.5% of unreacted phenylhydrazone remained. Aging the mixture for longer periods of time did not increase the assay yield of indolenine 8.

The reaction mixture was cooled to 12° C., and 7.0 L of MeOH was added. NaBH$_4$ was added in small (<20 g) portions maintaining the temperature below 15° C. The addition took 30 min. Moderate hydrogen evolution was observed during the addition, but it was easily controlled and there was virtually no frothing. Near the end of the addition the color rapidly changed from green to brown and then bright orange. A small amount (<200 mL) of a heavier phase had separated (presumably aqueous salts). HPLC analysis (conditions as before) indicated that all of the indolenine 8 had been consumed (90.4 area % CBZ-indoline 9); retention times: indolenine 8=7.5 min, indoline 9=8.2 min. TLC: ethyl ether as solvent, ceric sulfate-ammonium molybdate stain or 1% anisaldehyde stain; retention factors: indolenine 8=0.18, CBZ-indoline 9=0.33.

The color change from green to orange corresponds very closely to reaction end point. The quantity of NaBH$_4$ required to complete the reaction is heavily dependent on the temperature and rate of addition of NaBH$_4$, but the yield and quality of the product is virtually unaffected provided that the reaction is complete. The reaction mixture was cooled to 5° C. over a period of 30 min. Then 8 L of 3% aqueous NH$_4$OH (8 L) were added to bring the pH of the aqueous phase to 7.4, the mixture was agitated, and allowed to settle. The temperature rose to 15° C. The cloudy yellow lower aqueous phase was separated. The organic phase was washed with 4 L of 3% aqueous NH$_4$OH, 2×4 L of water, and 2×4 L of brine. The weight of the organic phase after the washings was 53.5 kg, and the assay yield was 94%.

The washed toluene solution was combined with the washed organic phases of two other similarly processed reactions. The total aldehyde used in the three reactions was 5.06 kg, (20.5 mol). The total weight of CBZ-indoline 9 assayed in the combined organic phases was 5.91 kg, (18.3 mol, 90% assay yield). The combined organic phases were dried with 5 kg of sodium sulfate, treated with 250 g of Darco G60 carbon for 30 min, and filtered through Solka-floc™. The filtrates were vacuum concentrated at 10 mbar at <25° C. until the residue was near dryness. The solvent switch was completed by slowly bleeding in 30 L of IPAC and reconcentrating to 14 L at 200 mbar at 50–60° C. The mixture was heated to reflux in order to obtain a clear homogeneous deep orange solution. $^1$H NMR analysis indicated that the solution contained ca. 6 mol % of residual toluene after solvent switch.

The solution was cooled to 68° C. and seeded with 4 g of crystalline CBZ-indoline 9. The solution was allowed to gradually cool to 26° C. over 6 h and aged for 9 h at 20–26° C. The slurry was cooled to 2° C. over 1 h and aged at 2° C. for 1 h. The product was isolated by filtration, and the filter cake was washed with 2×2 L of 5° C. IPAC and 2×2 L of 5° C. MTBE. The product was dried in the vacuum oven at 30° C. under a nitrogen bleed to give 4.37 kg (74%) of the title compound 9 as a light tan crystalline powder. HPLC analysis of the product indicated 99.5 area % purity. The mother liquor (11 L) and the washes contained 1.15 kg (19%) of additional product 9 and ca 3% of Cbz-isonipecotic acid phenylhydrazide (retention time=4.8 min).

EXAMPLE 5

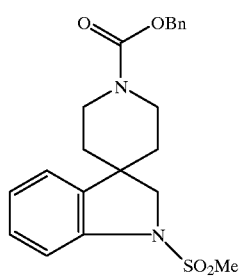

CBZ-Spiroindoline-methanesulfonamide (1)

| Materials: | |
|---|---|
| CBZ-Spiroindoline (9) | 1.69 kg (5.23 mol) |
| Methanesulfonyl chloride | 599 g (5.23 mol) |
| Et$_3$N (KF = 151) | 635 g (6.27 mol) |
| THF (KF = 41) | 12 L |

A 22 L flask was charged with the solid CBZ-spiroindoline 9 and then 11.5 L of THF and the Et$_3$N were transferred into the flask through a 10 μ inline filter. The resulting homogenous solution was cooled to 0° C. A 1 L dropping funnel was charged with the methanesulfonyl chloride and 500 mL of THF. The solution of the MsCl in THF was added to the reaction mixture maintaining the temperature between 0 and 4° C. The addition took 5 h and was exothermic. A white precipitate, presumably triethylammonium hydrochloride formed during the addition. HPLC analysis indicated that the reaction was complete at the end of the addition (9 was undetectable). HPLC conditions: 25 cm Dupont Zorbax RXC8 column with 1.5 mL/min flow and detection at 254 nm. Gradient Schedule:

| Time (min) | 0.1% aq. H$_3$PO$_4$:MeCN |
|---|---|
| 0 | 70:30 |
| 3 | 70:30 |
| 12 | 20:80 |
| 25 | 20:80 |

Retention times: 9=7.6 min, 1=13.6 min.

After the addition was complete the reaction mixture was warmed to 18° C. and aged for 16 h. There was no change in the appearance of the reaction mixture, and HPLC profile between the end of the addition and after the 16 h age. The reaction mixture was slowly transferred over 1 h into a vigorously stirred solution of 30 L of water and 200 mL of 37% aqueous HCl in a 50 L flask. The temperature in the 50 L flask rose from 22 to 28° C. The product separated as a pale tan gummy solid which changed to a granular solid. The aqueous suspension was cooled to 22° C. and aged for 1 h. The suspension was filtered, and the filter cake was washed with 2×4 L of MeOH/water (50/50). HPLC analysis indicated that <0.1% of the CBZ-Spiroindoline-methanesulfonamide 1 was in the mother liquors.

The filter cake was washed with 4 L of MeOH/water (50/50) to which 50 mL of 28% aqueous NH$_4$OH had been added. The filter cake was washed with 2×4 L of MeOH/water (50/50), and the solid was dried in the vacuum oven at 50° C. under a nitrogen bleed to give 2.03 kg (97%) of the title product 1 as an off-white powder. HPLC analysis of the solids indicated 93.7 area % 1.

EXAMPLE 6

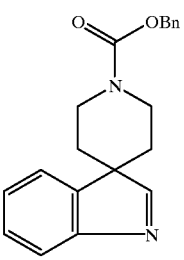

Optional Procedure for Isolation of Intermediate CBZ-Spiroindolenine (8)

| Materials: | |
|---|---|
| Piperidine-4-carboxaldehyde-1-benzyl carbamate (5) | 12.37 g (0.050 mol) |
| Phenylhydrazine | 5.41 g (0.050 mol) |
| Trifluoroacetic acid (TFA) | 11.56 mL, 17.10 g (0.150 mol) |
| Methylene chloride | 500 mL |

The CBZ-aldehyde 5 was dissolved in dichloromethane in a 1 L flask equipped with Teflon coated magnetic stirring bar. The resulting solution was cooled to 0° C. Phenylhydrazine was added via a weighed syringe over 5 min and the temperature was maintained at −1 to 3° C. while nitrogen was continuously bubbled through the reaction mixture.

TLC and HPLC analysis indicated complete consumption of the CBZ-aldehyde 5 and the appearance of a slight excess (<2%) of phenylhydrazine. TLC conditions: Silica, E. Merck Kieselgel G60 F254 0.25 mm; diethyl ether/pentane (4/1); and developing agent 0.5% ceric sulfate, 14% ammonium molybdate in 10% aqueous sulfuric acid then heat; Rf. aldehyde 5=0.52, phenylhydrazone 7=0.61, phenylhydrazine 6=0.21. HPLC conditions: 25 cm Dupont Zorbax RXC8 column at 30° C. with 1.0 mL/min flow and detection at 254 nm; gradient schedule:

| Time (min) | acetonitrile:water |
|---|---|
| 0 | 57:43 |
| 10 | 65:35 |

| Time (min) | acetonitrile:water |
|---|---|
| 15 | 75:25 |
| 18 | 75:25 | retention times: phenylhydrazine 6=4.5 min, toluene=7.2 min, phenylhydrazone 7=11.4 min.

The reaction mixture was aged for 10 min at 0–2° C., and TFA was added by syringe maintaining the temperature between 2 and 7° C. The reaction mixture was warmed to 35° C. over 30 min, and maintained for 17 h. The nitrogen sparge through the reaction mixture was stopped and a slow stream of nitrogen was maintained over the reaction mixture. During the first hour at 35° C. the color gradually darkened to a rosy pink then to a deep green, and a relatively small amount of a white crystalline precipitate (ammonium trifluoroacetate) formed. After aging for 17 h HPLC analysis (same conditions as above) indicated that the reaction mixture contained 93 area % indolenine 8 and <0.5% of unreacted phenylhydrazone remained. Aging the mixture for longer periods of time did not increase the assay yield of indolenine 8.

The reaction mixture was cooled to 10° C., and a mixture containing 60 mL 28–30% ammonium hydroxide, 90 mL water and 150 g crushed ice was added with good stirring. The color of the mixture changed to a salmon color. The organic phase was separated and washed twice with 400 mL water then 100 mL saturated aqueous NaCl. The organic phase was dried over magnesium sulfate and filtered through a plug of 5 g of silica. The filtrate was evaporated to give 15.84 g (99%) of indolenine 8 as a pale orange oil.

EXAMPLE 7

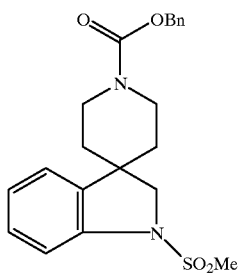

Procedure for the Preparation of CBZ-Spiroindoline-methanesulfonamide (1) without Isolation of Intermediate CBZ-Spiroindoline (9)

| Step 1: CBZ-Spiroindoline (9) | |
|---|---|
| Materials: | |
| Piperidine-4-carboxaldehyde-1-benzyl carbamate (5) | 49.5 g (0.20 mol) |
| Phenylhydrazine (Aldrich) | 23.7 g (0.22 mol) |
| Trifluoroacetic acid (TFA) | 75.4 g (0.66 mol) |
| Toluene (KF < 250 mg/L) | 654 mL |
| MeCN (KF < 250 mg/L) | 13.3 mL |
| NaBH$_4$ | 11.3 g, (0.30 mol) |
| Toluene | 20 mL |

| Step 1: CBZ-Spiroindoline (9) | |
|---|---|
| Materials: | |
| MeOH | 50 mL |

A 2% (by volume) solution of MeCN in toluene was made up using 654 mL of toluene and 13.3 mL of MeCN. In a 2 L 3 neck flask equipped with a mechanical stirrer 617 ml of the above solution were degassed by passing a fine stream of nitrogen through the solution for 5 min. Phenylhydrazine and TFA were added to the mixture while still degassing.

The CBZ-aldehyde 5 was dissolved in the rest of the solution prepared above (50 mL) and degassed by bubbling nitrogen through the solution while in the addition funnel. The solution in the flask was heated to 35° C., and the aldehyde solution was slowly added to the phenylhydrazine-TFA over 2 h. The mixture was aged at 35° C. for 16 h.

HPLC conditions: 25 em Dupont Zorbax RXC8 column at 50° C. with 1 ml/min flow and detection at 220 nm; isocratic 55% MeCN, 45% of 0.1% aqueous H$_3$PO$_4$. Typical HPLC profile after 16 h age:

| Retention time (min) | Area % | Identity |
|---|---|---|
| 1.6 | 0.1–0.5 | phenylhydrazine 6 |
| 4.1 | <0.1 | dimer 21 |
| 4.7 | <0.1 | aldehyde 5 |
| 5.0 | NA | spiroindoline 9 |
| 6.3 | NA | toluene |
| 6.9 | 97 | spiroindolenine 8 |
| 10.3 | <0.2 | phenylhydrazone 7 |
| | 2–3 tot. | other impurities <0.2% ea. |

The mixture was cooled to −10° C. and MeOH was added. A suspension of sodium borohydride in 20 mL toluene was added in small portions (1 mL) over 30 min taking care that the temperature did not exceed −2° C.

| Area % | Identity |
|---|---|
| 0.1–1 | phenylhydrazine 6 |
| 85–90 | CBZ-spiroindoline 9 |
| <0.1 | CBZ-spiroindolenine 8 |
| 10–15 tot. | other impurities (<3% ea.) |

The temperature was raised to 10° C. over 1 h, and 6% aqueous ammonia (200 mL) was added. The mixture was agitated for 10 min, allowed to settle for another 10 min, and the lower aqueous phase was drawn off. Acetonitrile (20 mL) and MeOH (20 mL) were added to the organic phase and it was washed with 150 mL of 15% brine. The organic phase was found to contain a 92% assay yield of CBZ-spiroindoline 9.

Step 2: CBZ-Spiroindoline-methanesulfonamide (1)

| Materials: | |
|---|---|
| CBZ-Spiroindoline (9)(MW = 322.51) | (0.184 mol) |
| Methanesulfonyl chloride | 21.1 g (0.184 mol) |
| DIEA (KF = 150 mg/L) | 29.7 g, 40.1 mL (0.230 mol) |
| THF (KF = 41 mg/L) | 150 mL |

The crude solution of CBZ-spiroindoline 9 solution from Step 1 above was concentrated in a 1L 3 neck flask (60–70° C., 150–200 Torr) until 250 g of residue remained. The THF and DIEA were added, and the resulting homogenous solution was cooled to 0° C. A 125 mL dropping funnel was charged with the methanesulfonyl chloride and 50 mL of THF. The solution of MsCl in THF was added over 2 h to the reaction mixture maintaining the temperature between 0 and 4° C. and the mixture was aged for 2 h at 5–8° C. The addition was slightly exothermic. A white precipitate, presumably DIEA-hydrochloride, formed during the addition. HPLC conditions were the same as above. HPLC analysis indicated that the reaction was complete 1 h after the end of the addition (9 was undetectable) and the assay yield was 94% from 9. Retention time: 1=7.8 min. Typical HPLC profile of reaction mixture after 2 h age:

| Area % | Identity |
| --- | --- |
| <0.1 | CBZ-spiroindoline 9 |
| 90–92 | CBZ-sulfonamide 1 |
| 8–10 tot. | other impurities (<2% ea.) |

The mixture was warmed to 20° C., and 200 mL of 1M aqueous HCl was added. The mixture was warmed to 50° C., and the aqueous phase was separated. The organic phase was washed sequentialy with 100 mL water, 100 mL 5% aqueous sodium bicarbonate, and 100 mL water. The organic phase was transferred to a 1 L 3 neck flask equipped for mechanical stirring and distillation. The mixture (ca 400 mL) was distilled at atmospheric pressure until 150 mL of distillate had been collected. The head temperature reached 107° C.; the pot temperature was 110° C. The distillation was continued with continuous addition of n-propanol at such a rate as to maintain a constant volume (ca 350 mL) in the pot. The distillation was stopped when a total of 525 mL of n-PrOH had been added and a total of 800 mL of distillate had been collected.

The temperature of both the head and pot rose from 94° C. to 98° C. during the solvent switch. Toluene and n-PrOH form an azeotrope boiling at 97.2° C. composed of 47.5% toluene and 52.5% n-PrOH. The mixture was allowed to cool gradually to 20° C. over 3 h and aged for 12 h. The mother liquor was found to contain 2% toluene and 4 mg/mL of sulfonamide. The solubility of the sulfonamide in various mixtures of toluene and n-PrOH has been determined by HPLC assay:

| % toluene in n-PrOH | solubility of 1 in mg/mL |
| --- | --- |
| 0 | 2.36 |
| 5 | 3.02 |
| 10 | 4.23 |
| 20 | 7.51 |
| 25 | 10.3 |

The crystalline slurry was filtered and washed with 3×100 mL of n-PrOH. The product was dried in a vacuum oven at 50° C. with a nitrogen bleed for 16 h to furnish 65.5g (82% from aldehyde 5) of 6 as a tan solid with 93.5 wt % purity.

| Area % | Identity |
| --- | --- |
| <0.1 | CBZ-spiroindoline 9 |
| >99 | CBZ-sulfonamide 1 |
| <1 tot.other impurities (<0.2% ea.) | |

For additional purification, a 40.0 g sample of the n-PrOH crystallized sulfonamide was dissolved in 134 mL of EtOAc at 60° C. and treated with 8.0 g of Darco G-60 carbon for 1 h at 60° C. After the addition of 2.0 g Solkafloc™, the slurry was filtered through a pad of 4.0 g Solkafloc™, and the pad was washed with 90 mL of EtOAc at 60° C. Prior to the addition of the carbon the solution was a brown color. The filtration proceeded well without plugging to give a golden yellow filtrate. The filtrate was distilled at atmospheric pressure in a 500 mL flask (pot temperature 80–85° C.) until 100 g (100 mL) of residue remained. This solution was allowed to cool to 35° C. over 3 h. Over a 1 h period, 116 mL of cyclohexane was added with good agitation at 35° C. The mixture was cooled to 20° C. over 1 h and aged at 20° C. for 12 h. At 35° C. much of the sulfonamide has crystallized out and the mixture was thick. Addition of cyclohexane at 20° C. makes agitation difficult. After the aging period, the supernatant was found to contain 2.5 mg 1/g. The crystalline slurry was filtered and the cake was washed with 77 mL of 2:1 cyclohexane-EtOAc and 2×77 mL of cyclohexane. The product was dried in a vacuum oven at 50° C. with a nitrogen bleed for 16 h to furnish 34.2 g of 1 (MW=400.3) as a white crystalline solid (85% recovery from crude 1, 70% from 5 with >99.9 wt % purity).

EXAMPLE 8

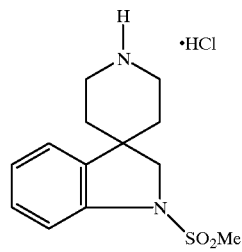

HCl Salt of Spiroindoline-methanesulfonamide (1a)

| Materials: | |
| --- | --- |
| CBZ-spiroindoline-methanesulfonamide (1) | 941 g (2.35 mol) |
| Pearlman's catalyst 20% Pd(OH)$_2$/C | 188 g |
| THF | 8 L |
| MeOH | 7 L |

The catalyst was suspended in 7 L of MeOH and transferred into the 5 gal autoclave followed by the solution of 1 in 8 L of THF. The mixture was hydrogenolyzed at 25° C. at 80 psi of H$_2$. After 2.5 h the temperature was raised to 35° C. over 30 min.

HPLC analysis indicated complete consumption of Cbz-spiroindoline-methanesulfonamide. HPLC conditions: 25 cm Dupont Zorbax RXC8 column with 1.6 mL/min flow and detection at 254 nm. Gradient Schedule:

| Time (min) | 0.1% aq. H$_3$PO$_4$:MeCN |
|---|---|
| 0 | 70:30 |
| 3 | 70:30 |
| 12 | 20:80 |
| 25 | 20:80 | retention times: Spiroindoline=7.6 min, Cbz-spiroindoline-methanesulfonamide=13.6 min.

The mixture was purged with nitrogen and the catalyst was removed by filtration through Solka-floc™ while still warm. The catalyst was washed with 4 L of THF and 2 L of MeOH. The pale yellow filtrates were concentrated to a thick oil at 10 mbar and <25° C. The solvent switch was completed by slowly bleeding in 15 L of EtOAc and reconcentrating to dryness. The residue solidified to a hard off-white mass. MeOH (1.5 L) was added and the mixture was heated to 70° C. to give a homogenous solution. While the solution was at 70° C., 10.5 L of EtOAc at 20° C. was added. The temperature fell to 40° C., and the mixture remained homogenous.

Subsequent experiments suggested that it is more convenient to solvent switch the MeOH-THF filtrates to MeOH, concentrate to the desired volume, and then add the EtOAc. This avoids the solidification of the residue upon concentration of the EtOAc solution.

Hydrogen chloride diluted with about an equal volume of nitrogen was passed into the solution. The temperature rose to 60° C. over the course of 15 min, and a white precipitate of the hydrochloride salt formed. Diluting the HCl with nitrogen only avoids the reaction mixture sucking back and may not be necessary.

The mixture was cooled in an ice bath, and the hydrogen chloride addition was continued for 1 h. The temperature gradually fell to 20° C. The suspension was aged for 2 h while the temperature was lowered to 10° C. The crystalline product was isolated by filtration, and the filter cake was washed with 3 L of EtOAc. It was dried in the vacuum oven at 35° C. to give 1.18 kg (86%) of the title product 1a as an off-white crystalline solid of >99.5 area % purity by HPLC analysis. HPLC conditions: 25 cm Dupont Zorbax RXC8 column with 1.5 mL/min flow and detection at 230 nm; isocratic 35% MeCN, 65% of 0.1% aqueous ammonium acetate. Retention time: 1a=5.4 min.

EXAMPLE 9

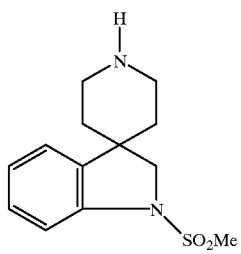

Spiroindoline-methanesulfonamide (Free base form) (15)

A 250 mL aliquot of the filtrate from the Cbz-hydrogenolysis containing 4.67 g of 1b (free base) was concentrated to ca 10 mL. The residue was dissolved in 20 mL of EtOAc and the solution was reconcentrated to ca 10 mL. This was repeated once more, and 10 mL of EtOAc was added to the residue. A crystalline precipitate began to form.

MTBE (20 mL) was added in one portion. Additional crystalline solid precipitated, but the supernatent still contained a substantial quantity of dissolved product which did not precipitate on standing. Hexanes (70 mL) were added dropwise over 2 h to the mixture with vigorous stirring. The slow addition of the hexanes is neccessary to avoid the oiling out of the amine.

The agitated mixture was aged for 1 h and filtered. The filter cake was washed with 20 mL of 1:1 MTBE-hexanes and then with 20 mL of hexanes. The product was dried under a stream of nitrogen to give 3.86 g (82%) of the free amine of 1b as an off white crystalline solid of >99.5 area % purity. HPLC conditions: 25 cm Dupont Zorbax RXC8 column with 1.5 mL/min flow and detection at 230 nm; isocratic 35% MeCN, 65% of 0.1% aqueous ammonium acetate. Retention time: 1b=5.4 min.

EXAMPLE 10A

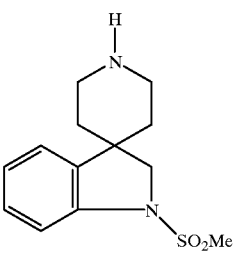

Spiroindoline-methanesulfonamide (Free base form) (15)

| Materials: | |
|---|---|
| CBZ-Spiroindoline-sulfonamide (1) | 833.5 gr (2.08 mol) |
| Pd(OH)$_2$/C (20% weight of Pd(OH)$_2$) | 124.5 (15%) |
| THF | 6.5 L |
| MeOH | 19.5 L |
| NH$_4$OH (conc) | 60 mL |

The hydrogenation was run three (3) times due to equipment limitations; this procedure refers to a single run. The CBZ spiroindoline sulfonamide1 was dissolved in THF (6.5 L, KF=53 μg/μL) and then MeOH KF=18 μg/mL, 4L) was added followed by addition of the catalyst and the slurry was transferred to a 5 gal autoclave. The remainder of the MeOH (2.5 L) was used for rinsing. The mixture was heated to 40° C. at 50 psi for 24 hours. The catalyst loading and reaction time are a function of the purity of starting material 1. This material was unique requiring ≧15% catalyst and long reaction time. Purer batches of spiroindoline required only 5% of catalyst and 4–6 hrs reaction time.

Upon completion (<0.1 A % 1 by LC) the mixture was filtered thru Solka Floc™ and the carbon cake washed with MeOH (13 L) containing NH$_4$OH (0.5%, 60 mL). The combined filtrates (assay shows 1587 g of spiroindoline amine 1b) were concentrated in vacuo and the resulting solids were partitioned between 40 L (of toluene:THF (3:1) and 0.5N NaOH (18 L). Although the layers separated easily a heavy precipitate could be seen in the aqueous layer. The aqueous suspension was thus extracted with CH$_2$Cl$_2$ (15 L). The aqueous and organic layer separated slowly. Prior to CH$_2$Cl$_2$ addition THF was added to the aqueous layer along with enough NaCl to saturate the layer. However dissolution of the product was not achieved which necessitated the use of CH$_2$Cl$_2$.

The combined toluene, THF and CH$_2$Cl$_2$ layers were combined and concentrated in the batch concentrator. The residue was flushed with 7 L of CH$_3$CN. Finally 10 L of CH$_3$CN were added and the solution stood overnight under N$_2$ atmosphere.

EXAMPLE 10B

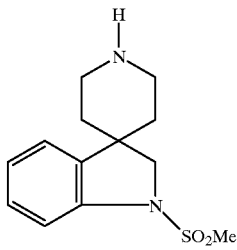

Spiroindoline-methanesulfonamide (Free base form) (15)

| Materials: | |
|---|---|
| CBZ-Spiroindoline-sulfonamide (1) | 3 kg (7.49 mol) |
| Darco G-60 | 600 g |
| Ethyl Acetate | 36 L |
| Absolute Ethanol | 189 L |
| 10% Pd/C | 450 g |
| Ammonia Solution | 500 ml |
| Solka Floc ™ | 2.5 kg |
| Isopropyl Acetate | 65 L |

A mixture of CBZ-spiroindoline (1) (1 kg) and Darco G-60 (200 g) in ethyl acetate (9 L) was stirred and heated at 60–65° C. under a nitrogen atmosphere for 8 hours. The Darco was removed by filtration at 60–65° C., the solid washed with hot ethyl acetate (3 L) and the filtrate and washings combined. LC wt/wt assay confirmed negligible loss to the Darco. The ethyl acetate solution was evaporated to dryness in vacuo using a 20 L Buchi apparatus and then flushed with absolute ethanol (2×5 L). This material was then slurried in absolute ethanol (8 L) warmed to 65–70° C. and placed in the 20 L autoclave. The batch was rinsed in with absolute ethanol (1 L). A slurry of 10% Palladium on charcoal (75 g, 7.5% by weight) in absolute ethanol (750 ml) was then added to the autoclave and rinsed in with a further portion of absolute ethanol (250 ml).

The batch was hydrogenated at 65° C. with vigorous stirring under 40 psi hydrogen pressure for 3 hours, a second portion of 10% palladium on charcoal (75 g) was added, the batch was hydrogenated for a further 2 hours and then sealed overnight. The batch was transferred (still hot, 60–65° C.) to a 20 L Buchi apparatus and degassed in vacuo to remove formic acid by "feeding and bleeding" absolute ethanol (18 L total).

This procedure was repeated twice more and the three batches were combined in a 10 gallon glass-lined vessel and the combined batch was degassed again by the addition and distillation (in vacuo) of absolute ethanol (2×10 L). Solka floc™ (0.5 kg) was added to the batch and rinsed in with ethanol (10 L). An Estrella filter was loaded with Solkafloc™ (2 kg) as a slurry in ethanol (20 L). The resulting mixture was warmed to 60–65° C. and then transferred at this temperature via heated filter using pump to two tared stainless-steel bins. The initial vessel, the filter, the pump and the lines were rinsed with a hot (60–65° C.) mixture of aqueous ammonia (500 ml) in absolute ethanol (25 L). The filtrate and washings were combined in the two stainless-steel bins.

The batch was then transferred to a vessel using an in-line filter containing a 10 micron cartridge, and then concentrated in vacuo to low bulk (~15 L). The ethanol was replaced by isopropyl acetate by the "feeding and bleeding" of 3× batch volumes of isopropyl acetate (45 L total), while maintaining a batch volume of ~15 L. The solvent switch, when complete, contained <1% residual ethanol by GC. The batch was then diluted to ~33 L by the addition of isopropyl acetate (20 L), and this solution of spiroindoline-amine 115(1.855 kg by LC analysis) in isopropyl acetate was used for the later steps-of the process.

EXAMPLE 11

O-Benzyl-D-Serine Methyl Ester Formation:

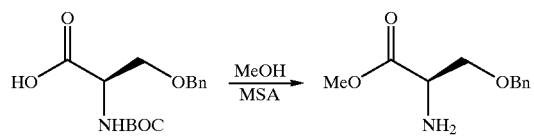

To a 5 L, 3-neck, round bottom flask, equipped with an overhead stirrer and a temperature probe, N-Boc-O-benzyl-D-serine (193 g, 0.62 mol) was added followed by methanol (1.93 L). Once a clear solution was obtained, methanesulfonic acid (186 mL, 4.6 eq; 2.87 mol), of 99.9% purity, was added over 15 min; a temperature increase to 35° C. was observed. After the acid addition reflux condenser was placed onto the apparatus along with a heating mantle. The reaction was heated to 50° C. and aged for 1.5 hours and increased its temperature to 65° C. for an additional 5–6 hours. The reaction progress was monitored by HPLC.

Upon reaction completion, the reaction mixture was solvent switched to iPAc (final volume of 2.6 L); complete removal of MeOH is necessary. To the iPAc solution, an aqueous solution of NaCl (15 wt %, 1.3 L) was added. While stirring, 2N NaOH solution was added over 1 hour to a pH of 9. Once at pH 9, a solution of more dilute base (0.5 N NaOH) was added carefully and slowly to a final pH of 10. [The temperature and pH were constantly being monitored; the observed temperature and pH ranges were 4–8° C. and 2.5–10.1, respectively.] The layers were separated and the iPAc volume was adjusted to the appropriate volume for the next reaction (20 volumes; 2.6 L). The assay yield was 133.3 g (97%).

HPLC conditions:

Column=Zorbax RX C-8 (250×4.6 mm)
Column temperature=48° C.
Flow rate=1.2 m,/min
Gradient solvent system=95:5%–10:90% of Buffer (0.05% H$_3$PO$_4$+0.01% triethylamine in water):Acetonitrile
Retention times: O-benzyl-D-serine=6.4 min (staring material) and O-benzyl-D-serine methyl ester=8.55 min (product).

EXAMPLE 12
N-Boc-Aminoisobutyric acid-O-Benzyl-D-Serine:

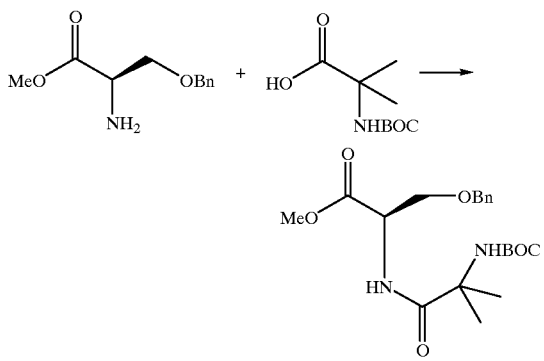

A solution of O-benzyl-D-serine methyl ester (130 g, 0.62 mol) from Example 11 in iPAc (2.6 L) was treated with HOBT (4 g, 0.05 eq; 0.03 mol), N-Boc-aminoisobutyric acid (126 g, 1.0 eq; 0.62 mol), water (1.3 L) and a solution of DCC (140.3 g, 1.1 eq; 0.68 mol) in iPAc. The reaction was aged at ambient temperature for 2 hours. After HPLC analysis indicated completion, the reaction mixture was quenched with 1.5 N HCl (700 mL) and aged for 1 hour (the observed pH was 1). After the age, the mixture was filtered through a pad of Solka Floc for DCU removal and the cake subsequently was washed with iPAC (6 volumes: 780 mL). The layers were separated and cut; the organic was washed with 1N NaOH (2 L). Once the layers were separated and cut, the organic (iPAc) layer was solvent switched into toluene (6.25 volumes). Assay yield: 223 g (91%).

HPLC conditions:
Column=Zorbax RX C-8 (250×4.6 mm)
Column temperature=45° C.
Flow rate=1.5 mL/min
Isocratic solvent system=50:50% of Aqueous buffer (0.1% $H_3PO_4$):Acetonitrile
Retention times: Starting material=1.6 min; HOBT=1.92 min; iPAc=3.23 min; Product=6.43 min.

EXAMPLE 13
N-Boc-Aminoisobutyric acid-O-Benzyl-D-serine:

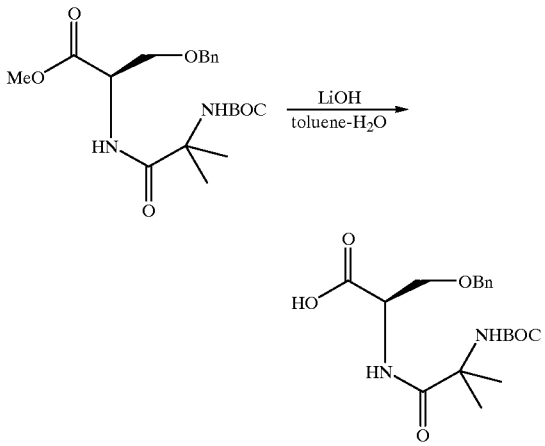

The toluene solution (6.25 mL toluene/g intermediate), which contained the methyl ester dipeptide intermediate (100 g, 0.25 mol) from Example 12, was transferred to a 2 L, 3-neck flask, equipped with a circulating bath, a mechanical stirrer, and a temperature probe. To the homogenous solution, deionized water (312.5 mL) was added and the temperature of the mixture was cooled to 4° C. To the cold biphasic solution; 2 N LiOH (312.5 mL) was added over 2 hours via syringe pump; this reaction mixture was then aged overnight at 4° C. After the reaction was judged complete by HPLC, the layers were separated and the aqueous was treated with iPAc (15 volumes: 1.5 L) followed by 1N HCl until the pH<2. The layers were separated and the organic was azeotroped to a KF of 500. The volume was adjusted to 1 L (10 volumes). The LC yield at this point was quantitative (96.4 g, 0.25 mol). The mixture in iPAc and heated to 65° C. At this temperature, DCHA (15 mL, 1.1 eq; 0.28 mol) in iPAc (2 volumes: 200 mL) was added. The resulting slurry was aged at 60° C. for 5 hours, then allowed to cool to room temperature where it was aged for 12 hours. The salt was filtered and washed with iPAc (4 volumes). The solid, thus obtained, was air dried and resuspended in iPAc (15 volumes; based on starting free acid) and 1M $H_2SO_4$ (10 volumes) was added. The layers were separated and the organic was washed again with 1M $H_2SO_4$ (10 volumes). The reaction mixture was aged for 30 min with vigorous stirring; the resulting two clear layers were separated and the organic was evaporated to a low volume (ca. 3 volumes of iPAC). The slurry was heated to 55° C. for ca. 1 hour and then cooled to ambient temperature. Heptane (9 mL/g of starting free acid) was added at that temperature and the resulting slurry was aged for 1 hour, filtered, and the cake was washed with heptane (4 volumes). The solid was dried in vacuo at 40° C.

HPLC conditions:
Column=Zorbax RX C-8
Column temperature=45° C.
Flow rate=1.5 mL/min
Isocratic solvent system=50:50% of Aqueous buffer (0.1% $H_3PO_4$):Acetonitrile
Retention times: Product=3.6 min; Toluene=6.0 min (overlap with starting material).

EXAMPLE 14

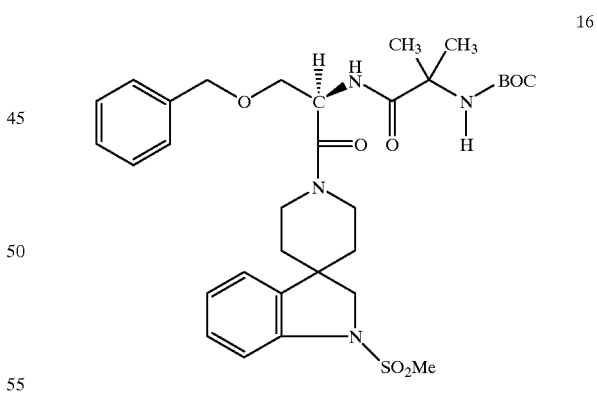

Boc-Aminoisobutyryl O-Benzylserine Spiroindoline (16)

The spiroindoline 15 (5 g; 19.8 mmol) from Example 10A/10B in acetonitrile (12.15 volumes: 61 mL) was treated with the dipeptide 14 (7.3 g; 1.02 eq; 19 mmol) from Example 13 followed by HOBT (2.8 g; 1.1 eq; 20.6 mmol) or HONB (N-hydroxy-5-norbornene-2,3-dicarboximide) (1.1 eq) at ambient temperature; both the substrate and the reagent were added as solids. The solution was then cooled to −25° C. and a DCC solution (4.7 g; 1.2 eq; 22.8 mmol) in acetonitrile (22.5 mL). was added over 30 min via syringe pump. The reaction mixture was aged overnight.

Upon completion (>95% conversion of 16 as indicated by HPLC analysis) of the reaction, 0.5 N HCl (110 mL; 11 vols based on 15) was added at −25° C. (but removed from the cooling bath) followed by iPAc (110 mL; 11 vols based on 15). The mixture was aged at room temperature for 15 minutes and then filtered to remove DCU. The filter cake was washed with iPAc (110 mL) and the biphasic filtrate was transferred into a separatory funnel where the layers were separated. The organic layer was washed with 1 N NaOH (110 mL) and the layers were separated. The organic layer was solvent switched to EtOH (final volume: 4 volumes based on assay yield for dipeptide-BOC 16: 100 mL) and seeded with 5 wt % of dipeptide-BOC 16 (1.2 g). The slurry was aged for 1 hour at 25° C. to establish a good seed bed followed by addition of heptane (4 volumes: 100 mL) over 2 hours. The mixture was aged at 25° C. for 1 hour, cooled to 0° C. slowly, and aged at that temperature overnight. The mixture was then filtered at 0° C. and washed with 1:1 EtOH-heptane (2 volumes: 50 mL) precooled at 0° C. followed by a room temperature heptane wash (4 volumes: 100 mL). The material was dried in a vacuum oven at 40° C. with a nitrogen sweep.

EXAMPLE 14A

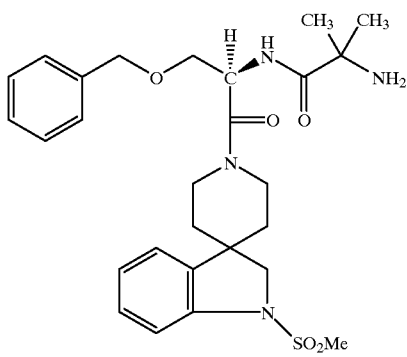

Aminoisobutyryl O-Benzylserine Spiroindoline (17)

| Materials: | |
|---|---|
| Boc Spiroindoline (16) | 3160 g (5.03 moles) |
| Methanesulfonic acid (MsOH) | 979 mL (15.1 moles) |
| EtOH | 6.2 L |
| H₂O | 30 L |
| 1N NaOH | 11 L |
| EtOAc | 26 L |
| Darco 60 activated carbon | 1 Kg |

The Boc spiroindoline 16 was dissolved in 6.2 L of EtOH and treated with MsOH (979 mL). The temperature rose from 20 to 30° C. and the reaction was allowed to proceed overnight. After 12 hours at 20° C. there was still 15 A % of starting material left so the mixture was heated to 35° C. for 6 hours. Upon completion (<0.1 A % 14) the reaction was cooled to 20° C. and 30 L of H₂O were added and the solution was filtered through a glass funnel with a polypropylene filter to filter off residual DCU. The mixture was transferred to a 100 L extractor and 26 L of EtOAc were added. The aqueous layer was basified via addition of chilled 1N NaOH (11 L) and 1 L of 50% NaOH. Addition of ice was required to keep the temperature below 14° C. Higher temperatures resulted in significant emulsion problems.

The organic layer was distilled at 50° C. at ca. 21" of Hg until KF<1000 μg/mL. Lower KF's result in more efficient carbon treatments and better recovery at the salt formation step. KF's of 160 μg/mL were achieved at the 700 g scale. The solution was diluted with ethyl acetate to a total volume of 31 L (LC assay 2.40 kg). Activated carbon (Darco G60) was added and the mixture was stirred for 24 h. The mixture was filtered through Solka Floc™ and the filter cake was washed with ethyl acetate (16 L), assay 2.34 Kg.

EXAMPLE 14B

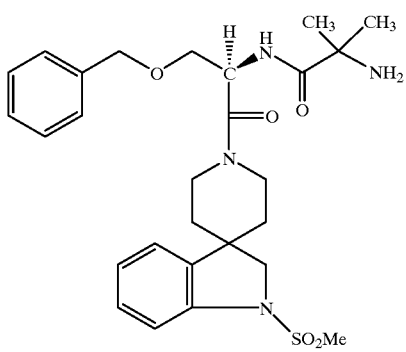

Aminoisobutyryl O-Benzylserine Spiroindoline (17)

| Materials: | |
|---|---|
| Boc Spiroindoline (16) | 4.395 kg (6.99 mol) |
| Methanesulfonic acid | 2.017 kg (20.99 mol) |
| Ethyl acetate | 185 L |
| 1M Aqueous sodium hydroxide | 16 L |
| 50% Aqueous sodium hydroxide | 2.6 L |
| Darco G-60 | 900 g |
| Solka Floc ™ | 2.5 kg |

Methanesulfonic acid (2.017 kg, 1.36 L, ~3 equivs.) was added to the stirred solution of the Boc spiroindoline 16 (4.395 kg) in ethanol (total volume ~25 L) in a reaction vessel at room temperature. The batch was warmed to 35–40° C., and stirred overnight. On the next day, the batch contained ~1.1 A % of starting material and so the reaction was continued for a further 4 hours, then LC showed ratio of product/starting material to be 99.6/0.4. The batch was concentrated in vacuo to ~15 L volume and then diluted with water (44 L). The batch was cooled to 5° C., stirred for 30 minutes and then filtered through a Sparkler in-line filter (containing a 10 m cartridge) using a pump to another vessel to remove a small amount of residual DCU.

The vessel, the pump, the filter and the lines were rinsed with water (10 L), and this was added to the vessel. Ethyl acetate (36 L) was added to the vessel and the stirred mixture was cooled to 10° C. A solution of cold (5–10° C.) 1M aqueous sodium hydroxide solution (16 L) and cold (5–10° C.) 50% aqueous sodium hydroxide solution (2.6 L) were added at 10° C. and the temperature rose to 14° C. The resulting mixture was stirred for 15 minutes at <14° C. and then the lower aqueous layer separated off.

The batch was concentrated in vacuo to ~20 L volume and then a mixture of ethyl acetate (35 L) and ethanol (5 L) was fed in while maintaining the volume at ~20 L. At the end of this distillation the KF was 9160 mgml$^{-1}$. The batch was solvent switched to ethyl acetate by "feeding and bleeding" ethyl acetate (40 L total). At the end of this distillation, KF was 446 mgml$^{-1}$. The batch was diluted with ethyl acetate (10 L).

Darco G60 (900 g) was added to the hazy mixture. This was rinsed in with ethyl acetate (6 L). This mixture was stirred at room temperature overnight. Next day, Solka Floc™ (0.5 kg) was added to the stirred batch in the vessel and then Solka Floc™ (2.0 kg) was stirred in a little ethyl acetate and loaded into an Estrella filter. The excess solvent was pumped away through a Sparkler in-line filter containing a 10m cartridge. The slurry was transferred from the vessel through a filter using a pump and then through another filter to 2×40 L stainless steel bins. Visual inspection showed the liquors to be clear and clean. The vessel was rinsed with ethyl acetate (22 L) and this was used to rinse through the route outlined above to the stainless steel cans. The contents of both cans was transferred into a reaction vessel and the solution was mixed thoroughly.

The batch (58 L) had a KF of 2950 mgml$^{-1}$ and so was redried by concentrating in vacuo to 20–25 L volume. The batch was diluted to 46 L volume (dipstick) by the addition of ethyl acetate (25 L). The KF was 363 mgml$^{-1}$. The batch was diluted to 62 L volume by the addition of ethyl acetate (17 L) and was used for the final stage of the process.

EXAMPLE 15A

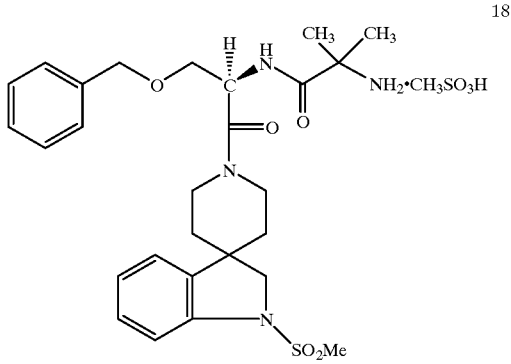

Spiro[3H-indole-3,4'-piperdin]-1'-yl)carbonyl]-2-(phenylmethyl-oxy)ethyl]-2-amino-2-methylpropanamide Methanesulfonate (18)

| Materials: | |
|---|---|
| Amine (17) | 2340 g (4.43 moles) |
| Methane sulfonic acid (MsOH) | 316 mL (4.88 moles) |
| EtOAc | 60 L |
| EtOH | 4.8 L |
| 8% EtOH in EtOAc | 20 L |

The volume of the solution of 17 from the previous step was adjusted to 60 L with ethyl acetate and EtOH (4.8 L) was added. The MsOH (316 mL) was added in 3 L of EtOAc at 45° C. To the deep red homogeneous solution was added 496 g of the title compound Form I seed (10% seed based on the weight of the free amine was employed). The temperature rose to ca. 48° C. and the reaction was aged at 52° C. for 1.5 hours. Analysis indicated complete conversion to the title compound (Form I). (At less than 10% seed longer age (>3 hours) was required). The slurry was allowed to cool to 20° C. overnight and was filtered in a centrifuge under N$_2$. The cake was washed with 20 L of 8% EtOH in EtOAc. N$_2$ is essential during filtration because the wet crystals are very hygroscopic. The batch was dried at 35° C. under vacuum to afford 2.7 Kg (56% overall yield) of the title compound (Form I) (99.9 A % purity; <0.1% enantiomer).

The conversion of Form II to Form I is also accomplished where the salt is formed in EtOAc-EtOH by addition of MsOH as above and the initial solution of the salt (at 55° C.) is cooled to 45° C. Crystals start appearing at that temperature and the slurry becomes thicker with time. The temperature is then raised to 51° C. and the slurry is aged overnight. Complete conversion to Form I of 18 should be expected. This procedure may also be employed to prepare seed crystals of Form I of 18.

EXAMPLE 15B

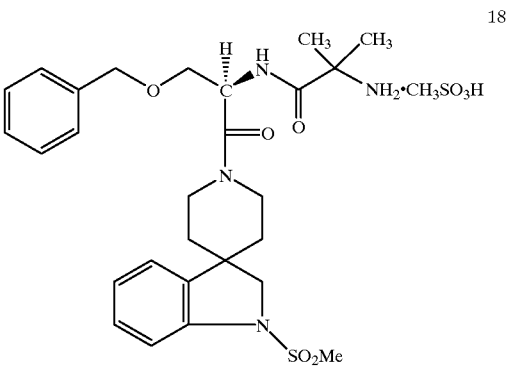

Spiro[3H-indole-3,4'-piperdin]-1'-yl)carbonyl]-2-(phenylmethyl-oxy)ethyl]-2-amino-2-methylpropanamide Methanesulfonate (18)

| Materials: | |
|---|---|
| Amine (17) | 3.1 kg (5.86 mol) |
| Methanesulfonic acid | 620 g (6.45 mol) |
| Ethyl acetate | 37 L |
| Absolute ethanol | 8.7 L |
| Spiro[3H-indole-3,4'-piperdin]-1'-yl)-carbonyl]-2-(phenylmethyl-oxy)ethyl]-2-amino-2-methylpropanamide methanesulfonate (Form I) | 70 g (0.11 mol) |

Absolute ethanol (6.4 L) was added to the solution of the amine (17) (3.1 kg) in ethyl acetate (total volume ~62 L) in a reacttion vessel. The batch was warmed to 50° C. and a solution of methanesulfonic acid (620 g, 412 ml, 1.1 equivs.) in ethyl acetate (11 L) was added over ~5 minutes at 50–54° C. The batch was seeded with spiro[3H-indole-3,4'-piperdin]-1'-yl)-carbonyl] -2-(phenylmethyl-oxy)ethyl]-2-amino-2-methylpropanamide methanesulfonate (Form I) (70 g) and the resulting slurry was stirred and heated at 55° C. under nitrogen atmosphere overnight.

The next day, the slurry was cooled to 15–20° C., held for 2 hours and then dropped to the 50 cm polypropylene filter under nitrogen atmosphere. The solid product was washed with a mixture of absolute ethanol (2.3 L) in ethyl acetate (26 L). The white, solid product was dug off and dried in an Apex oven in vacuo at 35° C. for an appropriate time (approx. two days). The dried spiro[3H-indole-3,4'-piperdin]-1'-yl)-carbonyl]-2-(phenylmethyl-oxy)ethy]-2-amino-2-methylpropanamide methanesulfonate (3.352 kg) was sieved using a Jackson-Crockatt sieve to give 3.347 kg (including seed, 70 g)} yield=3.277 kg.

Form I of N-[1(R)-[(1,2-dihydro-1-methanesulfonyl-spiro[3H-indole-3,4'-piperdin]-1'-yl)carbonyl]-2-(phenylmethyl-oxy)ethyl]-2-amino-2-methylpropanamide methanesulfonate is an anhydrous polymorph characterized by the following properties:

a melting point of 169° C. and solubility in isopropanol of 4.6 mg/mL.

The DSC curve for Form I of N-[1(R)-[(1,2-dihydro-1-methanesulfonyl-spiro[3H-indole-3,4'-piperdin]-1'-yl)carbonyl]-2-(phenylmethyl-oxy)ethyl]-2-amino-2-methylpropanamide methanesulfonate at 10° C./min in an open cup under nitrogen flow exhibits a single endotherm, due to melting, with a peak temperature of about 180° C. and an extrapolated onset temperature (melting point) of about 170° C. with an asociated heat of approximately 53 J/g.

Form I was characterized by an X-ray powder diffraction pattern with principal reflections at approximately: 6.5, 14.7, 16.9, 17.1, 17.9, 19.5, 21.1, 21.7, and 22.0° (2 theta). Data collected using a Philips APD3720 Automated Powder Diffraction instrument with copper Ka radiation. Measurements were made from 2° to 40° (2 theta) with the sample maintained at ambient room temperature.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, reaction conditions other than the particular conditions as set forth herein above may be applicable as a consequence of variations in the reagents or methodology to prepare the compounds from the processes of the invention indicated above. Likewise, the specific reactivity of starting materials may vary according to and depending upon the particular substituents present or the conditions of manufacture, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A process for the preparation of a compound of formula IV:

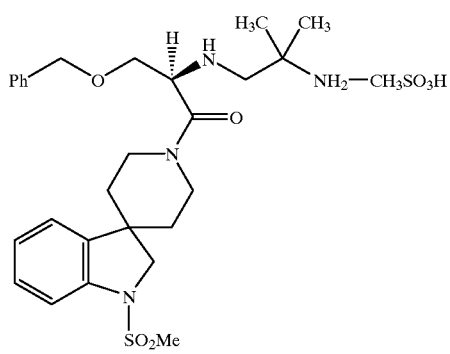

IV which comprises:

(1) coupling an amino acid of the formula:

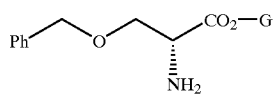

wherein G is a carboxyl protecting group, with a compound of the formula:

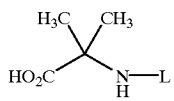

wherein L is an amino protecting group, in the presence of DCC in a first inert solvent in the presence of a first catalytic agent followed by removal of the carboxyl protecting group G to give a compound of formula I:

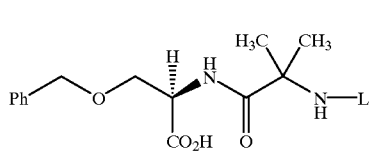

I wherein L is an amino protecting group, followed by:

(2) coupling the amino acid of the formula:

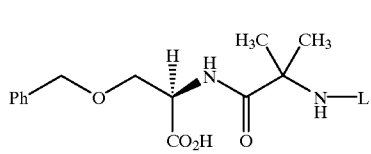

I wherein L is an amino protecting group, with a compound of the formula:

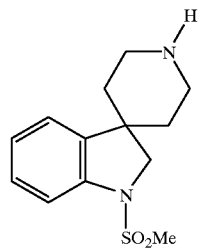

in the presence of DCC in a second inert solvent in the presence of a second catalytic agent to give a compound of the formula II:

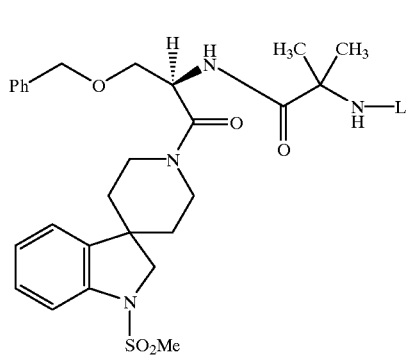

II wherein L is an amino protecting group, followed by:

(3) reacting the compound of the formula II with a second amino deprotecting agent to give a compound of the formula III, or a pharmaceutically acceptable salt thereof:

III

[Structure of compound III: Ph-O-CH2-CH(NH-C(=O)-C(CH3)2-NH2)-C(=O)-N connected to spiro piperidine-indoline with N-SO2Me]

followed by:
reacting the compound of the formula III with methanesulfonic acid to give the compound of formula IV.

2. A process for the preparation of a compound of formula I:

I

[Structure of compound I: Ph-O-CH2-CH(CO2H)-NH-C(=O)-C(CH3)2-NH-L]

wherein L is an amino protecting group, by coupling an amino acid of the formula:

[Structure: Ph-O-CH2-CH(NH2)-CO2-G]

wherein G is a carboxyl protecting group, with a compound of the formula:

[Structure: HO2C-C(CH3)2-NH-L]

wherein L is an amino protecting group, in the presence of DCC in an inert solvent in the presence of HOBT, followed by removal of the carboxyl protecting group G to give the compound of formula I.

3. The process of claim 2 wherein the solvent is selected from the group consisting of:
   acetonitrile; isopropyl acetate; ethyl acetate; propionitrile; water; chlorinated hydrocarbons; benzene; toluene; xylenes; and mixtures thereof.

4. The process of claim 3 wherein the solvent is selected from the group consisting of:
   isopropyl acetate:water; and acetonitrile.

5. The process of claim 2 wherein the temperature of the reaction is between 20 and 35° C.

6. The process of claim 2 wherein the compound of formula I, the amino protecting group is selected from:
   t-butoxy-carbonyl.

7. The process of claim 2 which is conducted in situ without isolation of the compound of formula I following its preparation.

8. The process of claim 1 wherein step (1) the first catalytic agent is HOBT.

9. The process of claim 1 wherein step (1) the first inert solvent is selected from the group consisting of:
   isopropyl acetate:water; and acetonitrile.

10. The process of claim 1 wherein step (1) the temperature of the reaction is between 20 and 35° C.

11. The process of claim 1 wherein the compound of formula I, the amino protecting group is selected from:
    t-butoxy-carbonyl.

12. The process of claim 1 wherein step (1) is conducted in situ without isolation of the compound of formula I following its preparation.

13. The process of claim 12 wherein step (2) the second catalytic agent is HOBT.

14. The process of claim 1 wherein step (2) the second inert solvent is acetonitrile.

15. The process of claim 1 wherein step (2) the temperature of the reaction is between −20 and −35° C.

16. The process of claim 1 wherein step (2) the second catalytic agent is HONB.

17. The process of claim 1 wherein step (2) the second inert solvent is isopropyl acetate:water.

18. The process of claim 17 wherein the solvent isopropyl acetate:water is in a ratio of approximately 40:60 to 60:40 (by volume).

19. The process of claim 18 wherein step (2) the temperature of the reaction is between 0 and 5° C.

20. The process of claim 1 wherein the compound of formula II, the amino protecting group is selected from:
    t-butoxy-carbonyl.

21. The process of claim 1 wherein step (2) is conducted in situ without isolation of the compound of formula II following its preparation.

22. The process of claim 1 wherein step (3) the second amino deprotecting agent is methanesulfonic acid.

23. The process of claim 1 wherein step (3) is conducted in a solution comprising ethanol.

24. The process of claim 1 wherein step (3) is conducted in situ without isolation of the compound of formula III following its preparation.

25. The process of claim 1 wherein the reaction of the compound of the formula III with methanesulfonic acid is conducted in a solution comprising ethyl acetate and ethanol.

* * * * *